(12) United States Patent
Fram et al.

(10) Patent No.: US 8,577,696 B2
(45) Date of Patent: Nov. 5, 2013

(54) SYSTEM AND METHOD FOR COMMUNICATION OF MEDICAL INFORMATION

(75) Inventors: Evan K. Fram, Paradise Valley, AZ (US); Murray A. Reicher, San Diego, CA (US); Christopher W. Lawson, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 301 days.

(21) Appl. No.: 12/622,269

(22) Filed: Nov. 19, 2009

(65) Prior Publication Data
US 2010/0299157 A1    Nov. 25, 2010

Related U.S. Application Data

(60) Provisional application No. 61/116,186, filed on Nov. 19, 2008.

(51) Int. Cl.
*G06Q 50/00* (2012.01)
(52) U.S. Cl.
USPC .................................................. 705/3; 705/2
(58) Field of Classification Search
USPC ........................................................ 705/2–3
See application file for complete search history.

(56) References Cited

U.S. PATENT DOCUMENTS

| 6,988,075 | B1 * | 1/2006 | Hacker | 705/3 |
| 2001/0016822 | A1 * | 8/2001 | Bessette | 705/3 |
| 2003/0204420 | A1 * | 10/2003 | Wilkes et al. | 705/3 |
| 2006/0230072 | A1 | 10/2006 | Partovi et al. | |
| 2006/0277075 | A1 * | 12/2006 | Salwan | 705/3 |
| 2006/0282408 | A1 * | 12/2006 | Wisely et al. | 707/3 |
| 2008/0059245 | A1 * | 3/2008 | Sakaida et al. | 705/3 |

FOREIGN PATENT DOCUMENTS

WO    WO 2007/131157 A2    11/2007

OTHER PUBLICATIONS

U.S. Appl. No. 12/437,522, filed May 7, 2009, Evan K. Fram.
Mendelson et al.; "Informatics in Radiology—Image Exchange: IHE and the Evolution of Image Sharing;" RadioGraphics, RSNA, 208; pp. 1817-1833.

* cited by examiner

*Primary Examiner* — Sind Phongsvirajati
(74) *Attorney, Agent, or Firm* — Leason Ellis LLP

(57) ABSTRACT

A system for transferring medical records from one or more source locations to a destination location is described. The system includes a plurality of medical site clients, each of which has access to medical records at a corresponding medical site, and an exam distribution server connected to each of the plurality of medical site clients via a network. The exam distribution server configured to receive an exam transfer request that specifies exam criteria and the destination location to which medical exams that have the criteria should be transferred. When the exam distribution server receives an exam transfer request, the server forwards the request to the medical site clients. When one of the medical site clients receives an exam transfer request, the medical site client sends all exam records meeting the criteria of the exam transfer request to the exam distribution server, and the exam distribution server forwards received exam records to the destination specified in the exam transfer request.

24 Claims, 28 Drawing Sheets

Fig. 26

SYSTEM AND METHOD FOR COMMUNICATION OF MEDICAL INFORMATION

PRIORITY CLAIM AND REFERENCE TO RELATED APPLICATION

The application claims priority under 35 U.S.C. §119 from prior provisional application Ser. No. 61/116,186, which was filed Nov. 19, 2008.

FIELD

A field of the invention is communication systems. Example applications of the invention include electronically transmitting medical images and examination records from one site to another.

BACKGROUND

Despite widespread availability of internet access and other means of high speed digital communication, medical imaging information is often moved through physical means. In the area of medical imaging, movement of imaging exams that used to occur on x-ray film now often occurs through production and mailing of data on a disk, such as a CD-ROM. While disks are less expensive to produce and transport than x-ray film, there are significant disadvantages. In addition to the expense associated with creation, transport, and management of physical media, there is also a resultant delay in information availability. This delay can have a negative impact on the quality and timeliness of patient care.

In addition to transport of physical media, some medical sites allow health care professionals to view medical images and exam information via a network such as the Internet. However, individual medical sites establish separate systems using separate login procedures. Thus, when a health care professional needs access to a patient's past medical exams, the health care professional must check each available medical site using separate accounts and disparate login procedures to complete a patient's medical history. Thus, the process for retrieving medical exam records, even via the Internet, can be time consuming and confusing. Accordingly, there is a need for better ways of communicating medical information to reduce costs, increase the speed of communication, and increase the efficiency of health care professionals involved in management of medical imaging information to more readily respond to patients' needs.

SUMMARY OF THE INVENTION

An embodiment of the invention is a system for transferring medical records from a source location to a destination location. The system includes a plurality of medical site clients that each has access to medical records at a corresponding medical site, and an exam distribution server connected to each of the plurality of medical site clients via a network. The exam distribution server is configured to receive an exam transfer request that specifies both criteria to determine whether exams should be transferred and the destination to which medical exams meeting specified criteria should be transferred. When the exam distribution server receives an exam transfer request, the server forwards the transfer request to each of the medical site clients. When the medical site clients receive the exam transfer request, each client sends all records stored at the corresponding medical site and meeting the specified criteria to the exam distribution server. The exam distribution server then forwards all received exam records to the destination specified in the exam transfer request.

Another embodiment of the present invention is a method of moving medical records from a source to a destination. The method uses a computer system including a plurality of medical site clients, and could also include one or more patient clients, and/or one or more doctor clients, all of the clients connected to an exam distribution server via a network.

BRIEF DESCRIPTION OF THE DRAWINGS

FIG. 26 is a GUI allowing a user to enter information regarding a package to be uploaded for use with the third embodiment of the present invention as shown in FIGS. 14 and 15;

DETAILED DESCRIPTION OF THE PREFERRED EMBODIMENTS

Figure 1:
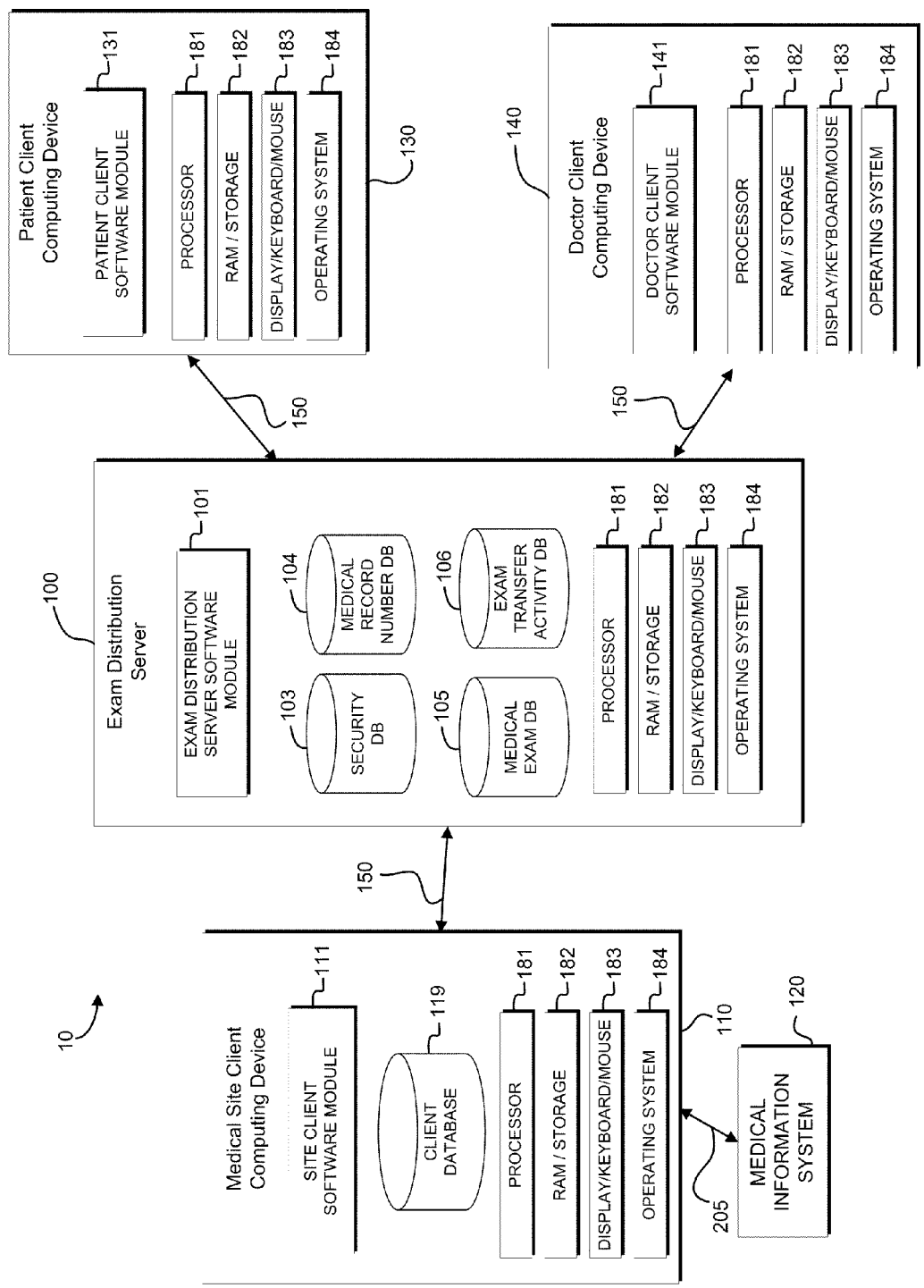
FIG. 1 shows a block diagram of a system for transferring medical records according to an embodiment of the present invention.

A system for transferring medical records from a source location to a destination location will now be described. The system includes a plurality of medical site clients, each client having access to medical records at a corresponding medical site. An exam distribution server is connected to each of the plurality of medical site clients via a network. The exam distribution server receives an exam transfer request that specifies criteria to determine whether exams should be transferred and the destination to which medical exams meeting specified criteria should be transferred. The exam distribution server forwards the exam transfer request to each of the medical site clients to which the exam transfer request is directed when the server receives an exam transfer request. When the medical site clients receive the exam transfer request from the exam distribution server, each of the clients sends all records that are stored at the corresponding medical site and meet the specified criteria to the exam distribution server. Also, the exam distribution server forwards all received exam records to the destination specified in the exam transfer request.

For purposes of this application, the term exam can mean any recorded medical information, including one or more of medical images, medical reports, demographic information relating to the patient, patient identification information, clinical information such as physician or other health care professional notes and lab data, physician orders, and scheduling requests for exams. Additionally, the term doctor, as used in this application includes doctors, nurses, technicians, technologists, file room personnel, and other health care professionals.

An embodiment of the invention is a system for electronically transferring exam information, including medical images, from one location to another. The system provides a better way to move medical images and exam information through electronic communication, reducing cost and increasing efficiency. Additionally, the system facilitates rapid communication of medical information between medical sites producing medical imaging exams, medical care facilities, doctors that interpret medical imaging exams, and patients. The communication system also reduces the potential for errors that may occur in matching medical information that exists in many disparate locations.

The system for communication of medical information advantageously can be used as a single portal for a doctor to view exams for his patients from any number of independent sites, and can be implemented to be a vendor-neutral system. Further, the system can be used as a communication device for transferring medical imaging exams between multiple medical sites in a way that complies with existing rules and regulations. The system is preferably compliant with internet standard transfer methods, such as file transfer protocol (ftp), hypertext transfer protocol (http), or the like. However, the system can be implemented using any existing protocols and transfer methods. The communication system advantageously provides those at a medical site an ability to send exams to a particular destination, as well as to retrieve exams from various sources. As such, the system facilitates remote examination review, such as for a teleradiology network or the like. Exams can be automatically routed to an appropriate health care professional for review based on, for example, time of day and/or specialty, among other factors.

Certain embodiments of the invention will now be discussed with respect to the drawings. The drawings may include schematic representations, which will be understood by artisans in view of the general knowledge in the art and the description that follows. Features may be exaggerated in the drawings for emphasis, and features may not be drawn to scale.

Turning now to FIG. 1, a medical exam communication system is designated generally at 10. The system 10 includes, for example, an exam distribution server 100, a medical site client computing device 110 (hereinafter, "medical site client"), a medical information system 120, a patient client computing device 130 (hereinafter, "patient client"), and a doctor client computing device 140 (hereinafter, "doctor client"). Only one of each of the medical site client 110, medical information system 120, patient client 130, and doctor client 140 is shown in FIG. 1, for ease of explanation. However, it will be appreciated by those of skill in the art that a plurality of each component may be present in the system.

The exam distribution server (EDS) 100 as shown in FIG. 1 is a server computer connected to a network 150. Alternatively, the EDS 100 includes a cluster of server computers, such as a cloud computing network. The EDS 100 runs an exam distribution server software module 101. The EDS 100 preferably includes a security database 103, a medical record number database 104, a medical exam database 105, and an exam transfer database 106, although alternate embodiments of the EDS may include more or fewer databases, and the database functionality may be spread across multiple server computers.

The security database 103 maintained by the EDS 100 stores exam authorization information, including regulation-compliant authorizations for transmission of an exam or access to an exam obtained from the patient. The medical record database 104 contains a record of successful matches of medical record number for patients among multiple medical sites. The medical exam database 105 includes one or more of medical exams, a list of medical exams stored on the EDS 100, a list of medical exams available at various medical sites configured to communicate with the EDS, and a list of exams scheduled to be performed at various medical sites configured to communicate with the EDS. The exam transfer activity database 106 maintains a record of exam transfer activity and access. Each of the databases 104-106 may be implemented using a relational database, a flat file database, an entity-relationship database, an object-oriented database, and/or a record-based database.

The medical site client 110 is a client computer configured to run a site client software module 111. The site client software module may be stored internally to the client 110, or maintained on a website accessed by the medical site client. The site client software module 111 allows for communication between the medical site client 110 and the EDS 100. Additionally, the medical site client 110 preferably includes a client database 119, which stores at least a listing of patients treated at the medical site.

Figure 2:
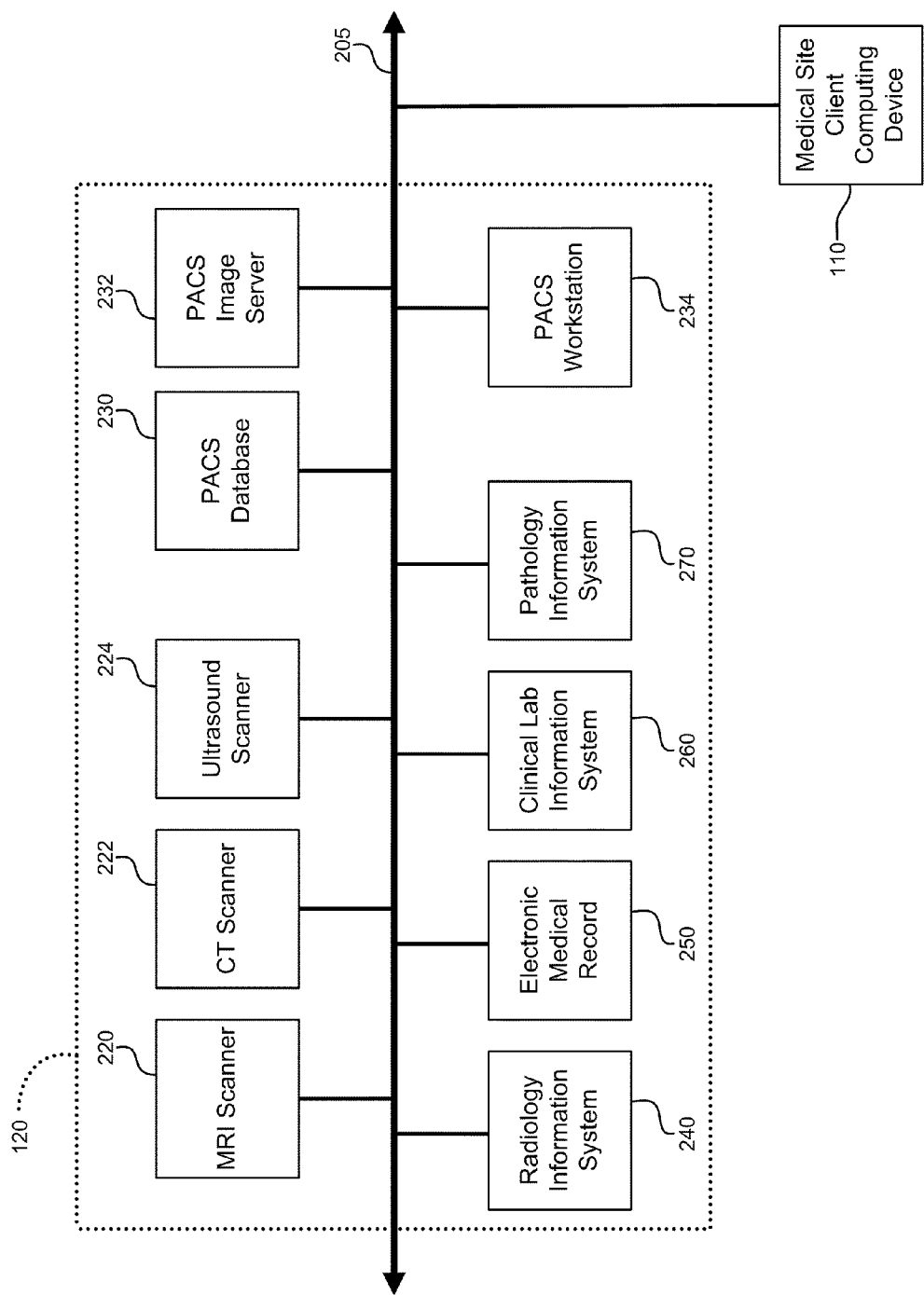
FIG. 2 shows a block diagram of the components of a medical information system for the system as shown in FIG. 1.

Further the medical site client 110 is in communication with the medical information system 120 via a data connection 205, such as a local area network (LAN), a wide area network (WAN), the Internet, or any other means for digital communication. As shown in FIG. 2, the medical information system 120 includes exam equipment capable of creating and/or storing medical images, such as a magnetic resonance imaging (MRI) scanner 220, a computed tomography (CT) scanner 222, and an ultrasound scanner 224. The medical information system 120 further includes one or more computer systems that manage medical information, such as a Picture Archive and Communication System (PACS) system having a database 230, image server 232, and workstation 234. The system 120 also includes a Radiology Information System (RIS) 240, an Electronic Medical Record (EMR) 250, a clinical lab information system 260, and a pathology information system 270. It is envisioned that the medical information system 120 could include additional exam equipment and computer systems without departing from the scope of the present invention. The various components 220-270 of the medical information system 120 communicate with one another using the data connection 205.

Returning to FIG. 1, the patient client computing device 130 is a client computer system running a patient client software module 131. The patient client software module 131 may be stored internally to the patient client 130, or maintained on a website accessed by the patient client.

Similarly, the doctor client computing device 140 is a client computer system running a doctor client software module 141. The doctor client software module 141 may be stored internally to the doctor client 140, or maintained on a website accessed by the doctor client.

Each of the EDS 100, medical site client 110, patient client 130, and doctor client 140 includes a processor 181, volatile and non-volatile storage 182, input and output devices 183, and an operating system 184. The processors 181 cause various software modules installed on the EDS 100, medical site client 110, patient client 130 and doctor client 140 to be run. The volatile and non-volatile memory 182 includes one or more computer readable storage medium, such as random access memory (RAM), read only memory (ROM), flash memory, a magnetic disk, an optical disk, magnetic tape, etc. The memory 182 stores programs resident on the computer systems 100, 110, 130, 140, such as the operating system 184 and the software modules 101, 111, 131, or 141. The input and output devices 183 provide an access point for users to interact with the computer systems 100, 110, 130, 140. As an example, the input and output devices 183 may include a visual display, a keyboard, and a mouse.

The medical site client 110, patient client 130, and doctor client 140 are each connected to the EDS via the network 150. The network 150 can include, for example a LAN, a WAN, or the Internet. Various communication protocols such as Digital Imaging and Communications in Medicine (DICOM), Health Level 7 (HL7), protocols defined by Integrating the Healthcare Enterprise (IHE), transmission control protocol/internet protocol (TCP/IP), or any other communication protocol is used to transfer data between the devices on the network 150.

Figure 3:
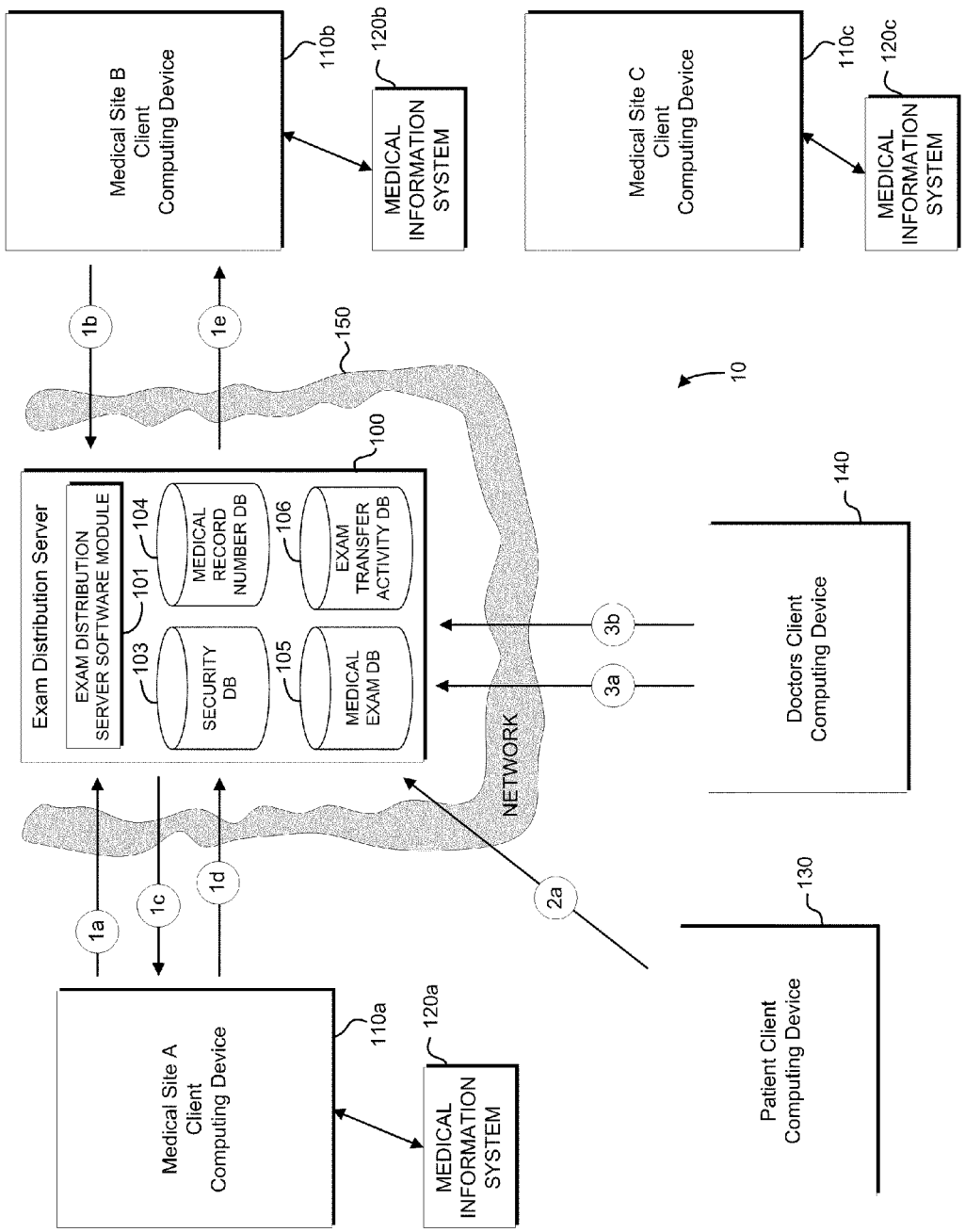
FIG. 3 shows a workflow diagram for a configuration of the system shown in FIG. 1.

Turning now to FIG. 3, a workflow describing steps required for Medical Site A client 110a to connect to and become authorized within the system is shown. First, in step 1a, the Medical Site A client 110a logs into the EDS 100 to establish an account with the EDS, where the Medical Site A client is the first account with the EDS. The account created with the EDS is stored in the security database 103 maintained by the EDS. Additionally, during the account creation process, Medical Site A client 110a preferably downloads software from the EDS and configures the software to communicate with medical information system 120a.

In step 1b, Medical Site B client 110b logs into the EDS 100 to create an account. As described above, the Medical Site B client 110b establishes an account with the EDS 100, which adds the account to the security database 103, and downloads software from the EDS, which is configured to communicate with medical information system 120b. Further, since other accounts exist within the security database 103 maintained by the EDS 100, the Medical Site B client 110b is presented with a list of other sites having an account with the EDS, and selects any number of sites to which a site communication invitation should be sent. In this case, the Medical Site B client 110b invites the Medical Site A client 110a to communicate.

The EDS then notifies the Medical Site A client 110a that the Medical Site B client 110b has joined the network and requested communication in step 1c. Then, in step 1d, the Medical site A client 110a accepts the invitation to communicate, such that the EDS is configured to allow transfer of information between Medical Site clients 110a and 110b. That is, the EDS 100 updates the security database 103 to indicate that Medical Site A client 110a and Medical Site B client 110b are able to communicate with one another. In step 1e, the medical Site B client 110b is notified that the site communication invitation was accepted by the Medical Site A client 110a.

In step 2a, a patient client 130 establishes an account with the EDS 100 and preferably downloads and configures software from the EDS. The EDS 100 updates the security database 103 to include the patient account. The patient account allows the patient client 130 to authorize medical sites and doctors to view patient information corresponding to the patient, as well as to transfer the patient information to other authorized sites. The patient may also view his medical information and view any activity related to access or transfer of his information recorded by the EDS 100.

In step 3a, a doctor client 140 establishes an account with the EDS 100. The EDS 100 updates the security database 103 to include the newly created account. The doctor client 140 then downloads and configures software from the EDS 100. The downloaded software allows the doctor client 140 to establish access rights to exams in step 3b. Information related to which exams the doctor may access is stored in the security database 103. By way of example, a doctor client may be granted access to all exams pertaining to a particular patient at one or more medical sites if the doctor is the patient's treating physician or ordering physician. Alternatively, the doctor may establish rights to all exams performed at a particular site, for example, if the doctor is practicing at the particular site.

Figure 4:
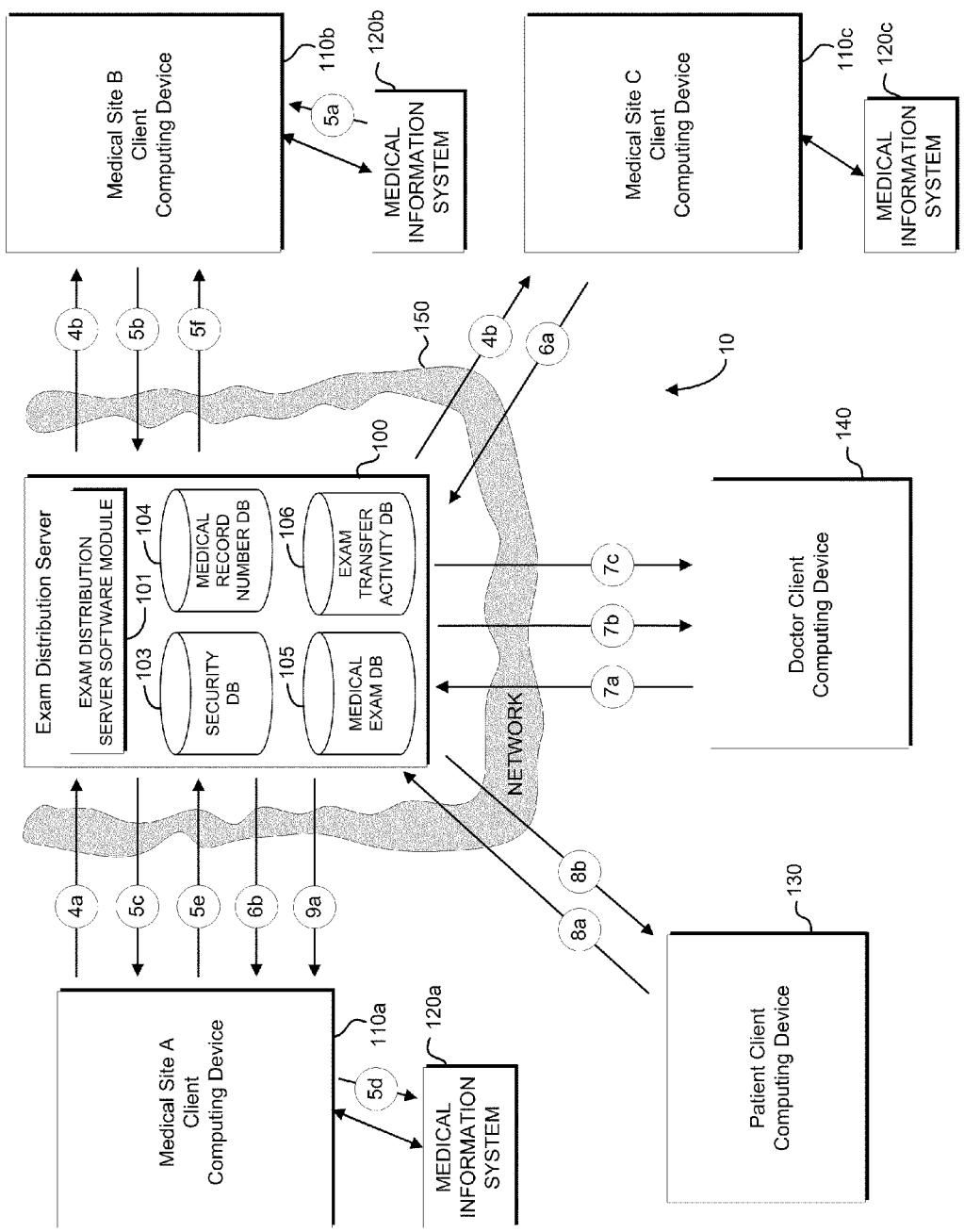
FIG. 4 shows a workflow diagram for communication between various components of the system of FIG. 1.

FIG. 4 shows a workflow diagram illustrating communication sent between various components of the system 10.

In step 4a, Medical Site A client 110a sends an exam transfer request (ETR) and an exam transfer authorization (ETA) to the EDS 100. The exam transfer request is an electronic message that directs the transfer of one or more exams from one or more source locations to a destination location. For example, an ETR may request transfer of exams from the EDS to a medical site client or doctor client, from a medical site client or doctor client to the EDS, or from one medical site client or doctor client to another. The ETR may be submitted, either manually or automatically, by a medical site client, a patient client, a doctor client, or the EDS. Further, the ETR may be submitted by one of the source location, the destination location, the EDS, a doctor client, or a patient client. In addition to specifying a destination location for the exams, the ETR also specifies criteria for exams to be transferred. For example, the criteria could include one or more of a patient name or medical record number, a range of dates on which the exam was conducted, a modality of the exam (i.e., CT scan, MRI, x-ray, etc.), a particular organ on which the exam was conducted, the ordering physician, exams marked as "STAT," exams with abnormal results, etc.

Then, in step 4b, the EDS 100 communicates the ETR and the ETA to each of the medical site clients that the Medical Site A client 110a is in communication with and to which the ETR and ETA are directed (e.g., Medical Site B client 110b and Medical Site C client 110c, as shown in FIG. 4).

In response to the ETR, Medical Site B client 110b retrieves exams that meet the criteria specified in the ETR from an associated medical information system 120b in step 5a. In step 5b, the Medical Site B client 110b then transmits the retrieved exams to the EDS 100. Additionally, the EDS 100 preferably retains the transmitted exams in the exam database 104. Then, in step 5c, the EDS 100 transfers the requested exams from Medical Site B client 110b and communicates the requested exams to the destination site indicated in the ETR (i.e., the Medical Site A client 110a, in FIG. 4).

When the Medical Site A client 110a receives the requested exams, the client transfers the exams to a corresponding medical information system 120a in step 5d. The Medical Site A client 110a then transmits an exam transfer request acknowledgement (ETRA) to the EDS 100 in step 5e. The ETRA is a message indicating the status of an exam transfer request, including information such as whether or not exams matching the exam transfer request are available, and whether or not the matching exams were successfully communicated. In step 5f, the EDS 100 transmits the ETRA to Medical Site B client 110b.

Additionally, when exams are transferred from site to site, medical record numbers for exams on one site are unlikely to match those of exams on the other site. Accordingly, medical record numbers can be matched to help ensure that the correct records are transferred. The medical records can be matched either automatically or manually, using additional patient information including one or more of a patient's full name, date of birth, gender, home address, telephone numbers, employer, insurance information, or the like. Medical record numbers may be matched at the exam source site (i.e., Medical Site B client 110b), at the EDS 100, or at the exam destination site (i.e., Medical Site A client 110a). When medical record numbers are matched automatically, it may be necessary to match some records manually if the result of the automatic matching is ambiguous. Once medical record numbers for a patient are matched, the matching medical record numbers are preferably stored in correspondence with one another in the Medical Record Number Database 104 for further use.

In steps 6a and 6b, a situation where no exams matching the ETR criteria are present at a medical site is explained. Specifically, in step 6a, Medical Site C client 110c sends an acknowledgment of the ETR to the EDS 100, indicating that no exams matching the criteria specified in the ETR are present at Medical Site C. Then, in step 6b, the EDS 100 sends the acknowledgement to the Medical Site A client 110a.

In steps 7a-7c, the situation where a client requests exams available from the EDS is explained. In step 7a, a doctor client 140 sends an ETR to the EDS 100, specifying criteria for requested exams. Then, in step 7b, the EDS 100 alerts the doctor client 140 that exams meeting the ETR criteria are available from the EDS. In step 7c, the exams are communicated from the EDS 100 to the doctor client 140. For example, the exams may be downloaded to the doctor client 140, or viewed directly from the EDS 100.

While steps 4a-4b assume that the medical site transmits both an ETR and an ETA, it is possible for the ETA to be transmitted separately. For example, the authorizing patient may transmit the ETA as shown in steps 8a and 8b. Specifically, in step 8a, a patient client 130 transmits an exam transfer authorization to the EDS 100, authorizing the transfer of the patient's exams. Then, in step 8b, the EDS 100 transmits an audit of all exam transfer activity relating to the patient's exams to the patient client 130. In some cases a physician or medical site may generate an ETA, for example where they are providing care to a patient and require the patient's prior medical records to provide that care.

Finally, if the service provided by the EDS 100 is a pay-per-use service, the EDS sends billing information to a client that sent an ETR. For example, after resolution of the ETR sent by the Medical Site A client 110a in steps 5, the EDS sends billing information to the Medical Site A client in step 9a. Alternatively, the patient or medical site could be billed for transfers of a patient's medical information, regardless of which client requested the information transfer.

Figure 5:
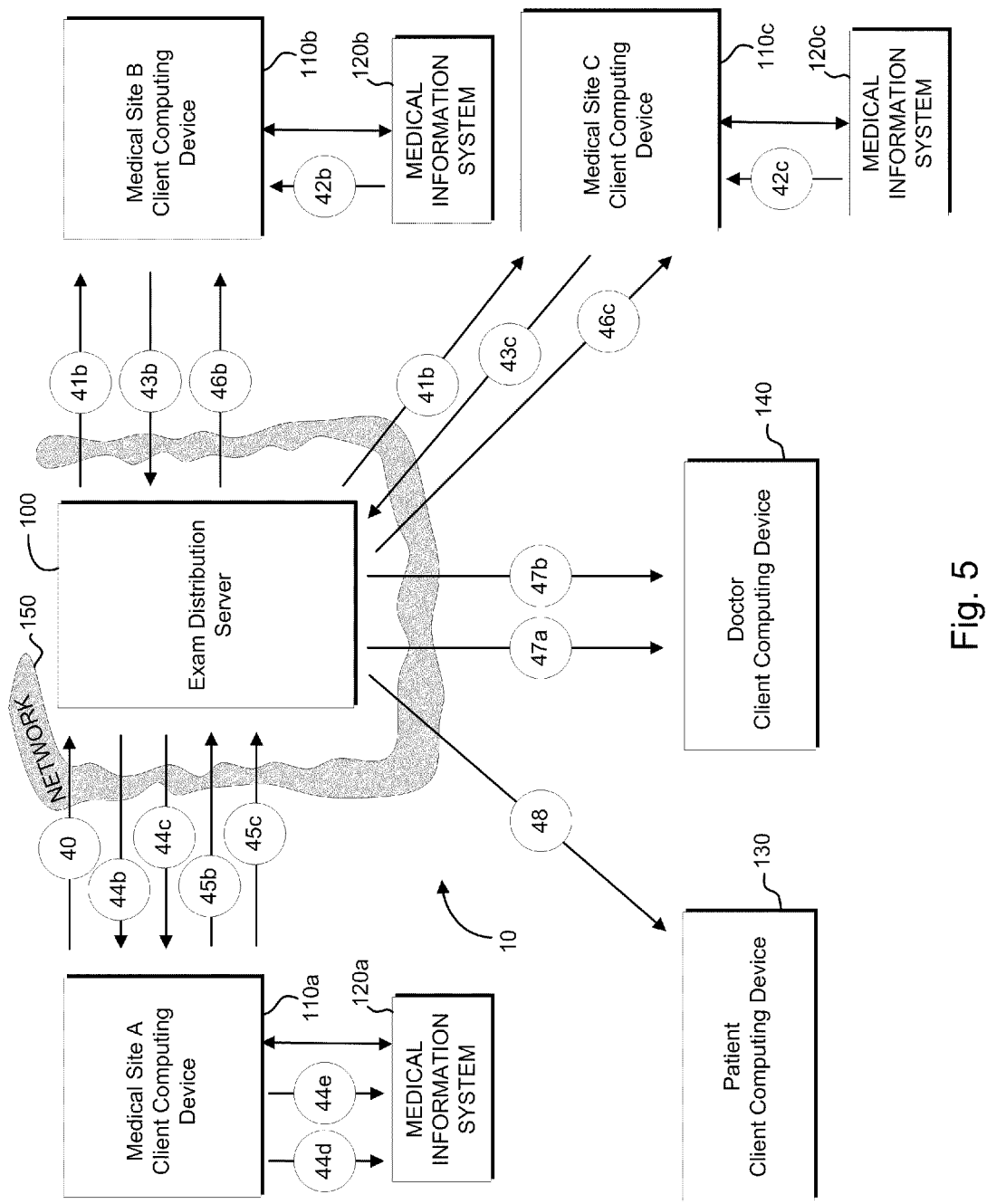
FIG. 5 shows a workflow diagram illustrating the communications taking place in the system from FIG. 1 when a patient is admitted to one medical site and has prior exams retrieved from another site.

Turning now to FIG. 5, a workflow example where a patient's prior exams are retrieved when the patient is admitted to a medical site is shown. In step 40, Medical Site A client 110a transfers an ETR to the EDS 100, requesting transfer of all prior exams for a patient "John R. Smith." An ETA may be transferred with the ETR, or it may already exist in the security database 103 maintained by the EDS 100. In steps 41b and 41c, the EDS 100 transmits the ETR and ETA to Medical Site B client 110b and Medical Site C client 110c, respectively. Then, in steps 42b and 42c, Medical Sites B and C query their respective medical information systems 120b and 120c to retrieve exams that meet the criteria specified in the ETR. Next, Medical Sites B and C transfer the requested exams to the EDS 100 in steps 43b and 43c. Then, in steps 44b and 44c, the EDS 100 transfers exams from Medical sites B and C to the Medical Site A client 110a.

In steps 44d and 44e, the Medical Site A client 110a stores the exam results from Medical Sites B and C in associated medical information system 120a. Once the exam results are properly stored, Medical Site A client sends ETRAs to the EDS 100 indicating receipt of exams from Medical Sites B and C respectively, in steps 45b and 45c. Then, in steps 46b and 46c, the EDS 100 forwards the ETRAs to Medical Site B client 110b and Medical Site C client 110c, respectively.

In step 47a, the EDS 100 send a notification to a doctor client 140 that the patient's exams are available for access. Then, in step 47b, the doctor client 140 accesses the exams, either by downloading the exams from the EDS 100 or by accessing the exams directly from the EDS. Finally, in step 48, the EDS 100 transfers a notification of activity regarding the patient's exams to a patient client 130.

Figure 6A:
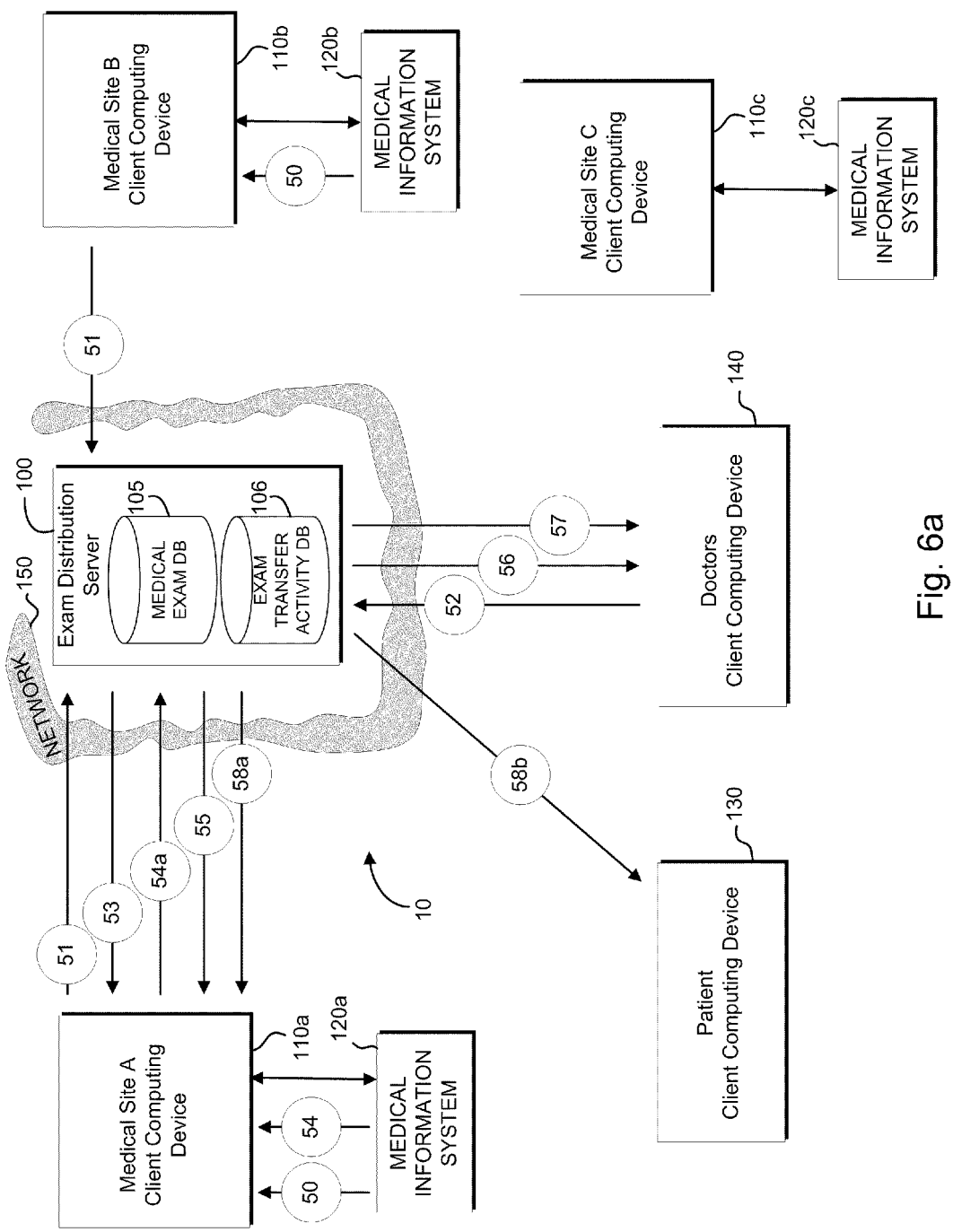
FIG. 6a shows a workflow diagram illustrating an example of communications taking place in the system from FIG. 1 when a doctor uses the system as a portal to access patient information from multiple medical sites.

Turning to FIG. 6a, a work flow diagram illustrating an example of communications taking place in the system 10 when a doctor uses the system as a portal to access patient information from multiple medical sites is shown. In step 50, Medical Site A client 110a and Medical Site B client 110b query their respective medical information systems 120a and 120b for new exams. This process is performed at various time intervals, or more preferably periodically. Alternatively, the medical information systems 120a, 120b are configured to send new exams to Medical Site A client 110a and Medical Site B client 110b, respectively. Then, in step 51, the Medical Site A client 110a and Medical Site B client 110b transfer a list of new exams to the EDS 100. These exam lists are preferably stored in Medical Exam DB 105, which may be configured to store lists of medical exams available at each of the medical sites configured to communicate with EDS 100.

In step 52, a doctor client 140 transfers a standing exam transfer request (SETR) to the EDS 100. Alternatively, the doctor may create a SETR by interacting with the EDS via a web client. The SETR is stored in the exam transfer activity database 106 maintained by the EDS 100 to monitor incoming lists of new exams at one or more medical sites that meet certain criteria and perform certain actions when those criteria are met. For example, a SETR might indicate that all exams on patients where a particular physician is the ordering physician or consulting physician are to be transferred to the EDS. Further, the SETR preferably features automatic notification sent to the particular physician when new exams meeting the established criteria are available. As another example, an SETR might indicate specify that all brain and spine MRI scans performed between 7 AM and 5 PM are to be transferred to a particular doctor and/or a particular site for reading.

In step 53, when the EDS 100 receives a list of new exams from Medical Site A client 110a containing an exam that meets the criteria of the SETR, the EDS sends an ETR to the Medical Site A client for the exams meeting the standing ETR criteria.

As a result of the ETR, the Medical Site A client 110a retrieves the requested exam from the corresponding medical information system 120a in step 54. Then, in step 54a, the requested exam is transferred from the Medical Site A client 110a to the EDS 100. In step 55, an ETRA is sent from the EDS 100 to the Medical Site A client 110a.

In step 56, the EDS 100 notifies the doctor client 140 that a new exam is available for his patient. In other embodiments, the notification sent from the EDS 100 may occur through other means, such as by email, text message, or via pager. Then, in step 57, the doctor is able to access the new exam, either by downloading the exam or by accessing the exam directly from the EDS 100. Once the doctor client 140 views the exam, the EDS transmits an ETRA to the Medical Site A client 110a indicating that the exam has been viewed in step 58a. The ETRA may be stored, for example, in the client database 119 as shown in FIG. 1. A record of the doctor client 140 accessing the exam is stored in Exam Transfer Activity DB 106 of EDS 100. In step 58b, the patient is notified of the exam transfer and viewing activity.

Figure 6B:
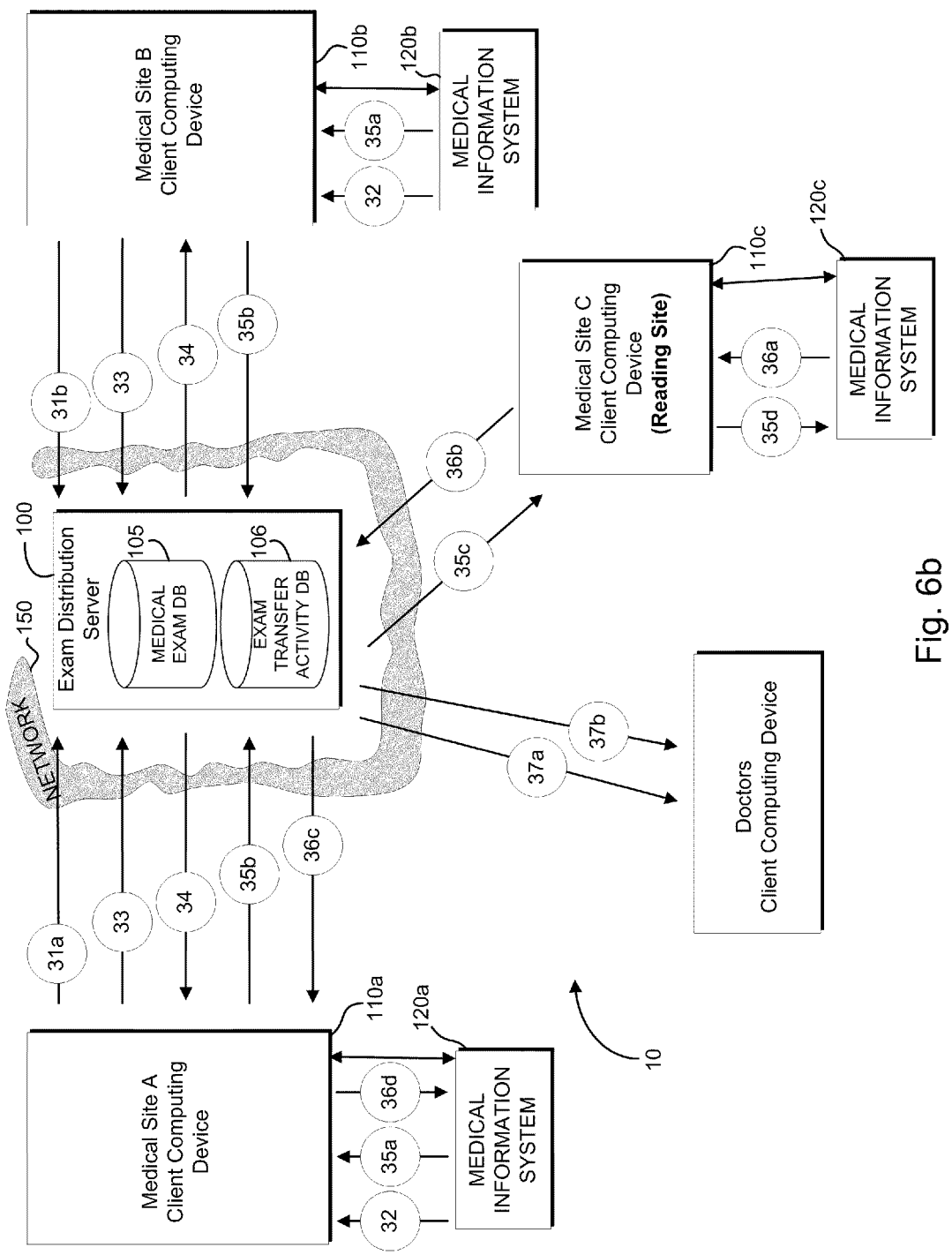
FIG. 6b shows a workflow diagram illustrating an example of communications taking place in the system from FIG. 1 when the system is facilitating operation of a radiology reading network.

Turning now to FIG. 6b, a workflow diagram illustrating an example of communications taking place in the system 10 when the system is facilitating operation of a radiology reading network. In this example, the Medical Site C client 110c operates as a reading site.

In steps 31a and 31b, Medical Site A client 110a and Medical Site B client 110b transmit a SETR to the EDS 100 directing the EDS to route exams meeting the criteria of the SETR (e.g., new, unread exams) to reading site 110c. Alternatively, the SETR may be created in response to activity by the reading site 110c. Then in step 32, Medical Site A client 110a and Medical Site B client 110b query their respective medical information systems 120a and 120b for new exams and in step 33, lists of new exams are transferred to the EDS 100.

The EDS 100 evaluates the list of exams to determine which exams meet the criteria for the SETR, and then communicates an ETR to each of the medical client sites for new unread exams that should be transferred to the reading site 110c in step 34. In response to the ETRs issued by the EDS 100, the Medical Site A client 110a and Medical Site B client 110b retrieve the requested exams from their respective medical information systems 120a and 120b in step 35a. Then, in step 35b, the exams are communicated from the Medical Site A client 110a and Medical Site B client 110b to the EDS 100. Once the EDS 100 receives the requested exams, the exams are forwarded to the reading site 110c in step 35c. Exams are then transferred from the reading site client 110c to its associated medical information system 120c in step 35d.

Next, new exam results are read at the reading site stored in the medical information system 120c, and communicated to the reading site client 110c in step 36a. Then in step 36b, reading site client 110c transmits an ETR to route the exam results to the originating medical site client (in this case, Medical site A client 110a), and the ETR and new exam results are transmitted to the EDS 100. In step 36c, the EDS transmits the new exam results, such as a doctor's report of the results of the exam, to the originating site client (Medical Site A client 110a), and in step 36d the new exam results are communicated from the Medical Site A client 110a to the medical information system 120a.

In a preferred embodiment, a doctor client 140 corresponding to the physician ordering the exam is notified that exam results have been received in step 37a. Notification methods include email, text messaging, pager messaging, and the like. Then in step 37b the doctor client accesses the exam result.

Figure 7:
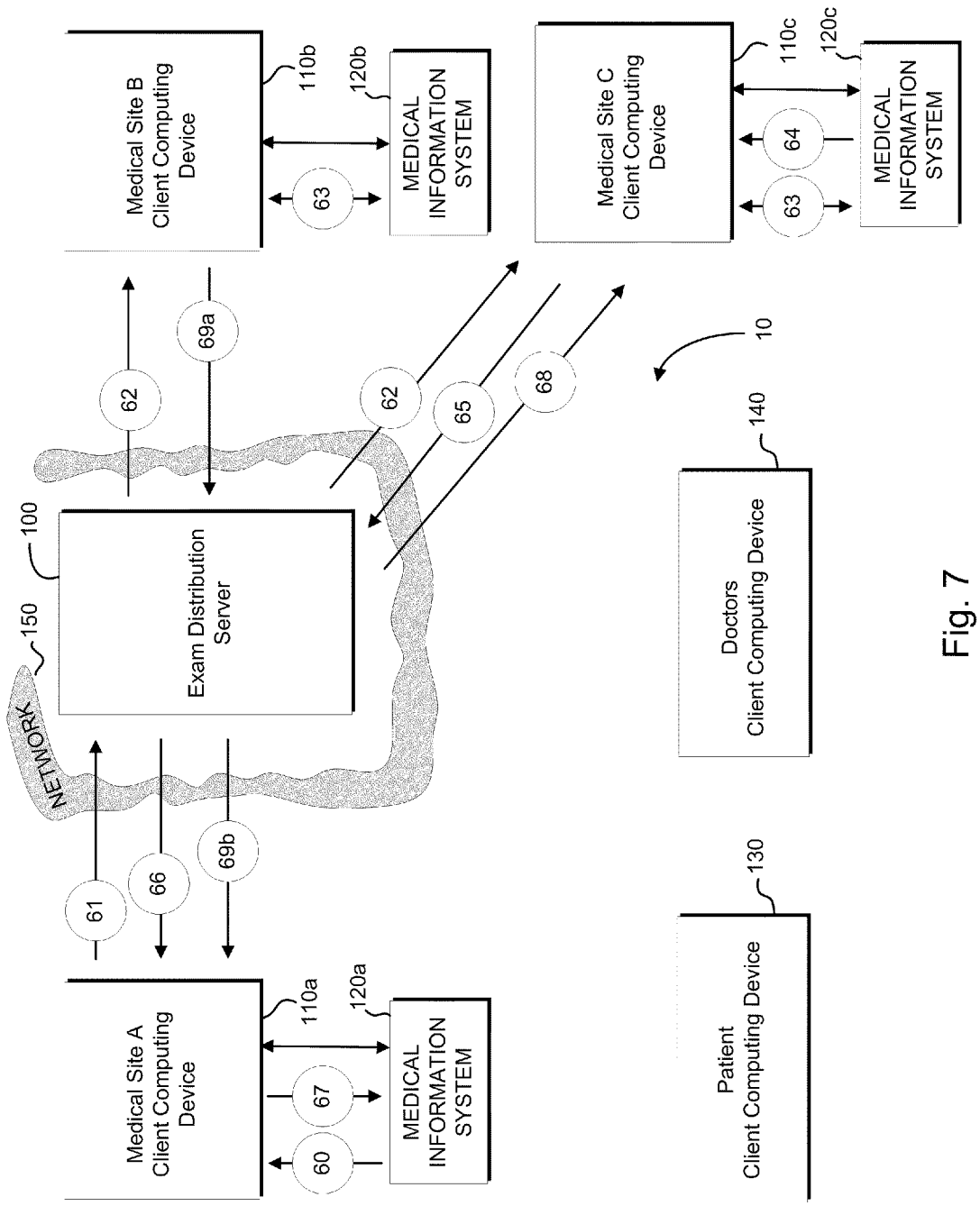
FIG. 7 shows a workflow diagram illustrating an example of communications taking place in the system from FIG. 1 when a patient undergoes an imaging exam at one medical site and prior relevant exams are automatically retrieved from other medical sites.

FIG. 7 shows an example workflow illustrating communications taking place in the system 10 when a patient undergoes an imaging exam at one medical site and prior relevant exams are automatically retrieved from other medical sites. When a patient is schedule for an exam at Medical Site A, the scheduled exam is entered into the medical information system 120a. The medical information system notifies the Medical Site A client 110a of the scheduled event in step 60.

In response to the scheduled event, Medical Site A client 110a transfers an ETR and ETA to the EDS 100 requesting transfer of prior exams from all other sites for the patient in step 61. Then in step 62, the EDS 100 transfers the ETR and ETA to all sites configured to communicate with Medical Site A (i.e., Medical Site B client 110b and Medical Site C client 110c). Alternatively, the EDS 100 may keep a comprehensive list of all exams maintained at each of the medical sites in Medical Exam DB 105, and send the ETR and ETA to only those sites which have exams that meet the criteria specified in the ETR.

In step 63, Medical Site B client 110b and Medical Site C client 110c each query their respective medical information systems 120b, 120c for exams meeting the criteria specified by the ETR. In this example we assume that only Medical Site C has relevant exams. The Medical Site C client 110c retrieves relevant exams from its associate medical information system 120c in step 64 and transfers the retrieved exams to the EDS 100 in step 65. Then, in step 66, the retrieved relevant exams are transferred from the EDS 100 to Medical Site A client 110a. Then the Medical Site A client 110a communicates exams received in response to the ETR to the associated medical information system 120a in step 67. The EDS 100 sends an ETRA to the Medical Site C client 110c indicating that Medical Site A client 110a successfully received the exams in step 68.

In response to the ETR, the Medical Site B client 110b sends an ETRA to the EDS 100 in step 69a indicating that no matching exams were found at Medical Site B. The EDS 100 then forwards the ETRA to the Medical Site A client 110a in step 69b.

Figure 8:
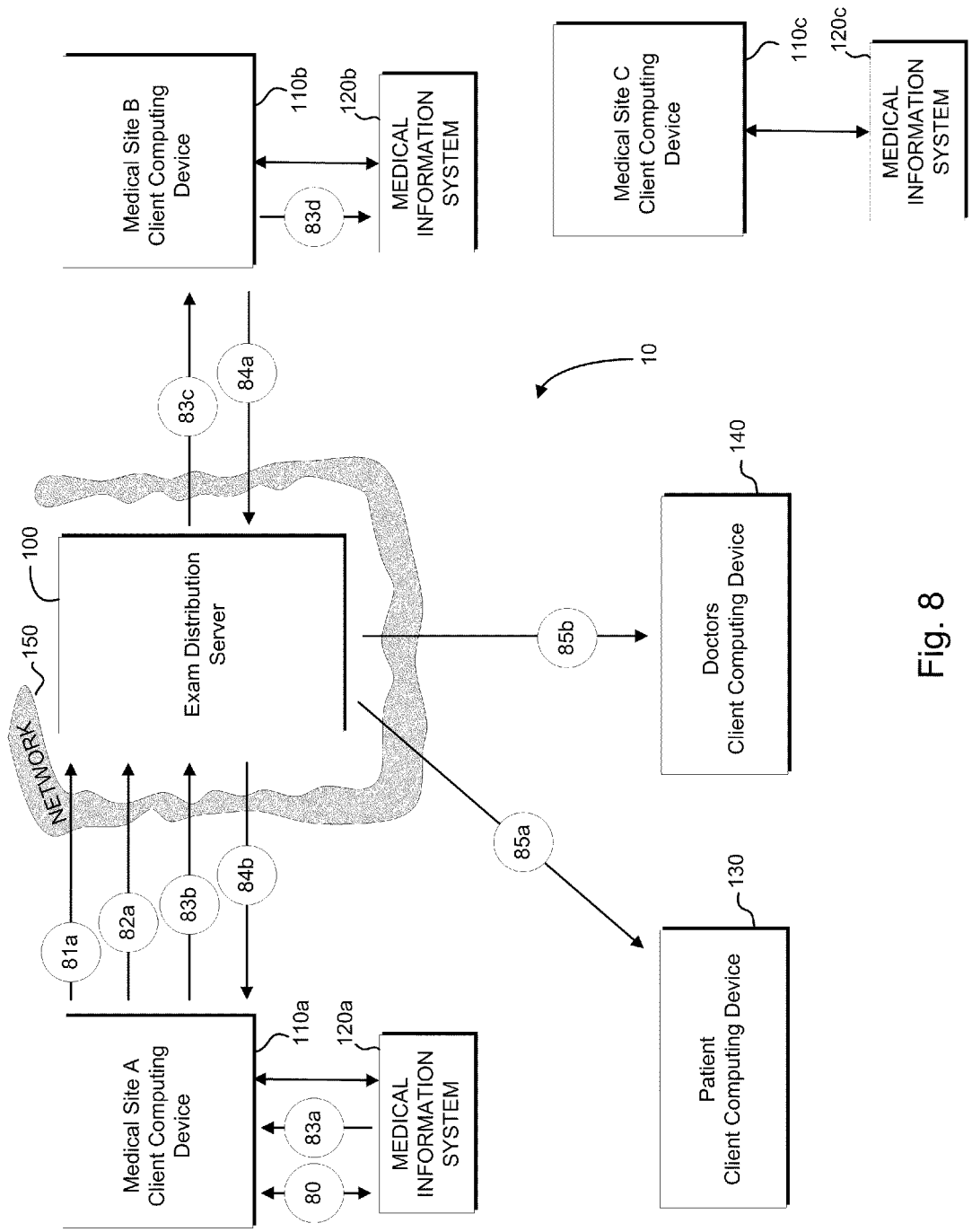
FIG. 8 shows a workflow diagram illustrating an example of communications taking place in the system of FIG. 1 when an exam is manually transferred from one medical site to another.

Turning now to FIG. 8, a workflow diagram illustrating an example of communications taking place in the system 10 when an exam is manually transferred from one medical site to another is shown. In step 80, a user at Medical Site A client 110a queries the local medical information system 120a for a desired exam. Then, in step 81a, Medical Site A client 110a creates an ETR instructing the EDS 100 to transfer the desired exam from Medical Site A to Medical Site B, and transmits the ETR to the EDS. The Medical Site A client 110a also transmits and sends to the EDS 100 an ETA authorizing transfer of the exam to Medical Site B in step 82a.

In step 83a, the Medical Site A client 110a retrieves the exam from the medical information system 120a. Then, in step 83b, the Medical Site A client 110a uploads the exam to the EDS 100. The EDS 100 transfers the exam to the Medical Site B client 110b in step 83c. Then the exam is placed in medical information system 120b in step 83d.

After the exam is received at Medical Site B, the Medical Site B client 110b sends an ETRA to the EDS 100 in step 84a indicating that the exam was successfully received. In step 84b the EDS 100 forwards the ETRA to the Medical Site A client 110a. Additionally, the EDS 100 makes exam transfer activity available to the patient client 130 in step 85a and notifies the doctor of the availability of the transferred exam in step 85b.

Figure 9:
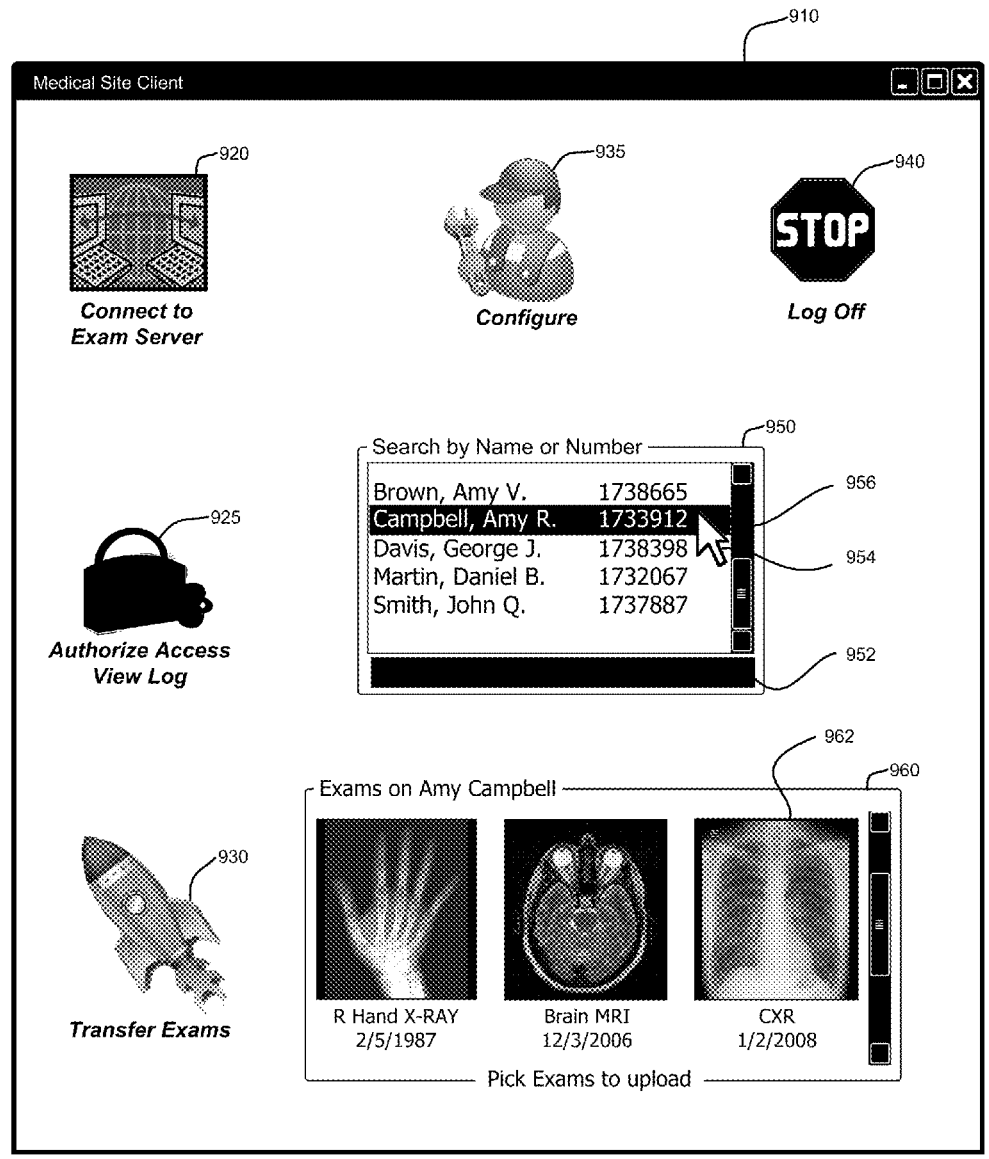
FIG. 9 shows a sample screenshot of a graphical user interface for a medical site client for the system of FIG. 1.

FIG. 9 shows an example graphical user interface (GUI) 910 for the site client software module 111 executed by the medical site client computing device 110 as shown in FIG. 1. The GUI 910 includes a plurality of icons and informational windows allowing a health care professional to interact with the client 110.

A "Connect to Exam Server" icon 920, when clicked, causes the software module to initiate a connection to the exam distribution server 100 using authentication information entered by the user and/or stored by the client 110. This connection can be used to create an account with the EDS 100, as described in FIG. 3.

Icon 925, labeled "Authorize Access and View Log," when clicked, allows a health care professional to view, modify, and transmit exam authorization information. Additionally, the health care professional can view exam transfer activity for exams that he is authorized to view. The user is preferably also able to view billing information relating to the communication system through icon 925.

A "Transfer Exams" icon 930 allows a health care professional to initiate transfer of exams and messages between the client 110 and the EDS 100. Additionally, the health care professional can input information regarding transfer of local exams to other sites and request that exams be transferred from other medical sites. The icon 930 also allows the health care professional to create and transmit ETRs and SETRs.

A configure icon 935 allows a health care professional to configure various options through additional menus. The user can configure communication settings between the medical site client 110 and the associated medical information system 120 by, for example configuring the communication protocol (e.g., HL7, DICOM, IHE, etc.) used to send data between the client and the information system or by adjusting setting particular to the selected protocol. The health care professional can also configure settings related to uploading lists of new exams to the EDS 100. The configure icon 935 also provides a menu used to initiate and accept invitations to communicate with other sites and doctors using the EDS 100, as discussed above.

The GUI 910 includes a Log Off icon 940 and a patient search box 950. The Log Off icon 940 is used to terminate the connection between the client 110 and the EDS 100. The patient search box 950 allows a health care professional to choose an exam from the local medical information system 120 to transfer to another medical site. The health care professional may type a patient name or medical record number into an input box 952, or use a cursor 954 to browse and select from a full list of patients in the view box 956.

An exam choice interface 960 allows a health care professional to view all exams associated with a patient selected in the patient search box 950. The health care professional can select an exam by clicking on a thumbnail image 962 representative of the exam. Alternatively, the health care professional may click on the exam description located below the thumbnail image 962 to select the exam.

Figure 10:
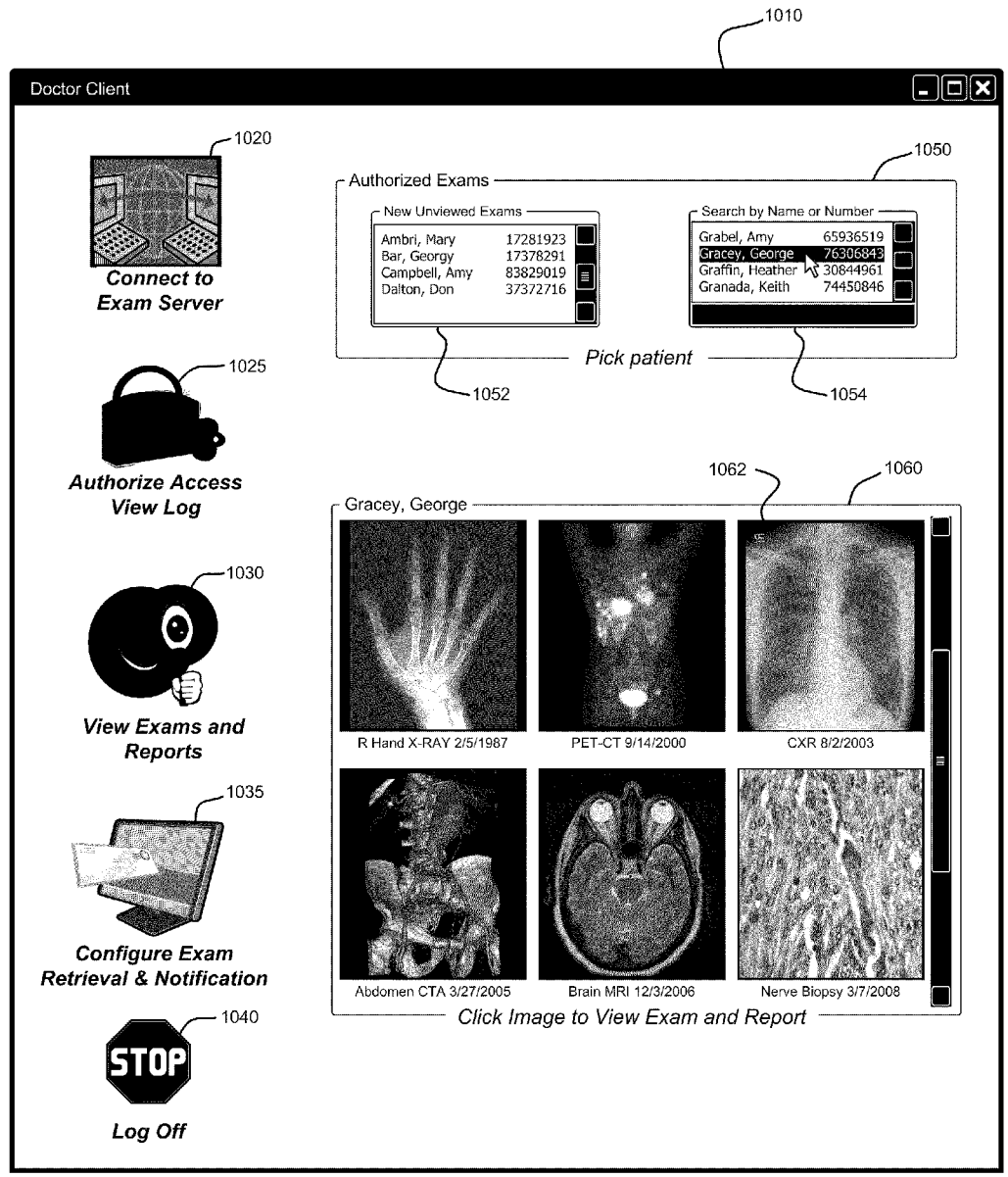
FIG. 10 shows a sample screenshot of a graphical user interface for a doctor client for the system of FIG. 1.

FIG. 10 shows an example GUI 1010 for the doctor client software module 141 executed by the doctor client computing device 140 as shown in FIG. 1. The GUI 1010 includes a plurality of icons and informational windows including a connect to exam server icon 1020, an authorize access and view log icon 1025, a view exams and reports icon 1030, and configure exam retrieval and notification icon 1035, a log off icon 1040, a patient search interface 1050, a new unviewed exams interface 1052 and an exam choice interface 1060, allowing a doctor to interact with the client 140.

The "connect to exam server" icon 1020 initiates a connection between the doctor client 140 and the EDS 100. Additionally, through additional menus, the doctor can establish an account with the EDS 100.

The "authorize access and view log" icon 1025 allows the doctor to view, modify, and transmit exam authorization information in the form of an ETA. The icon 1025 also allows the doctor to view exam transfer activity and billing information.

Clicking the "view exams and reports" icon 1030 provides the doctor with an interface that allows the doctor to search for and view exams, including images and reports. For example, this icon may cause the patient search interface 1050 and the exam choice interface 1060 to appear in the GUI.

The "configure exam retrieval and notification" icon 1035 provides the doctor with an interface to configure automatic notification and/or retrieval of exams related to the doctor's patients. Additionally, the icon 1035 allows the doctor to generate an ETR and/or a standing ETR.

The "log off" icon 1040 and the patient search interface 1050 are now explained. Clicking the "log off" icon 1040 terminates the connection between the client 140 and the EDS 100. The patient search interface 1050 includes the new unviewed exams interface 1052, which provides a list of new unviewed exams that the doctor is authorized to view, and a patient search box 1054 that provides a searchable list of all exams on the EDS that the doctor is authorized to view. The list of new unviewed exams 1052 lists all patient having new exams that the doctor has not viewed and is authorized to view. The patient search box 1054 allows the doctor to search through a full list of his patients by patient name or medical record number.

The exam choice interface 1060 displays all exams pertaining to a selected patient. For example, the interface may contain thumbnail images 1062 representative of each exam, which can be selected to view the full exam.

Figure 11:
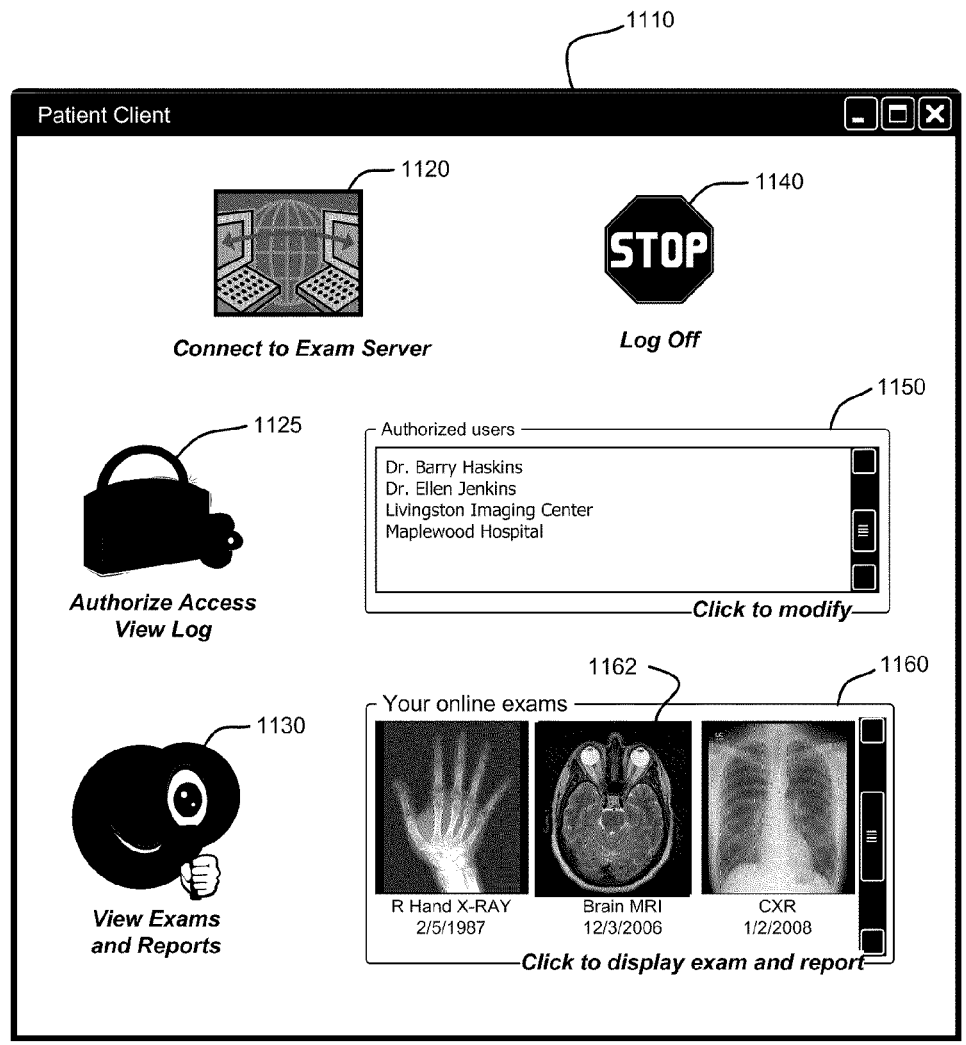
FIG. 11 shows a sample screenshot of a graphical user interface for a patient client for a system of FIG. 1.

FIG. 11 shows an example GUI 1110 for the patient client software module 131 executed by the patient client computing device 130 as shown in FIG. 1. The GUI 1110 includes a plurality of icons and informational windows including a connect to exam server icon 1120, an authorize access and view log icon 1125, a view exams and reports icon 1130, a log off icon 1140, an authorization interface 1150, and an exam choice interface 1160, allowing a patient to interact with the client 130.

The "connect to exam server" icon 1120 initiates a connection between the patient client 130 and the EDS 100. Additionally, the icon preferably allows the patient to view additional menus used in creating an account with the EDS 100.

Clicking the "authorize access and view log" icon 1125 allows the patient to view, modify, and transmit exam authorization information in the form of an ETA, for example by revealing the authorization interface 1150 in the GUI 1110. Additionally, the icon 1125 allows the patient to view exam transfer activity, viewing activity and billing information.

The "view exams and reports" icon 1130 provides a user interface to view and search for exams and reports pertaining to the patient. For example, clicking the icon may cause the display of the exam choice interface 1160 in the GUI 1110.

The "log off" icon 1140 and the authorization interface 1150 are now explained. The "log off" icon 1140 terminates the connection between the patient client 130 and the EDS 100. The authorization interface 1150 allows a patient to authorize doctors and medical sites to view and transfer medical information pertaining to the patient. This information can be viewed and/or modified by the patient whenever the patient client 130 is connected to the EDS 100.

The exam choice interface 1160 displays a list of exams pertaining to the patient, including images and reports. The patient may choose to view any of the displayed exams by clicking a thumbnail 1162 representative of the exam.

Two additional embodiments will be described that allow communication of medical information from one site to another, for example using an exam distribution server that is accessible via the Internet. The second embodiment, related to exam workflow, will be described in reference to FIGS. 12, 13, and 16-23. The third embodiment, related to file/package workflow, will be then described with reference to FIGS. 14, 15, and 24-32.

Figure 12:
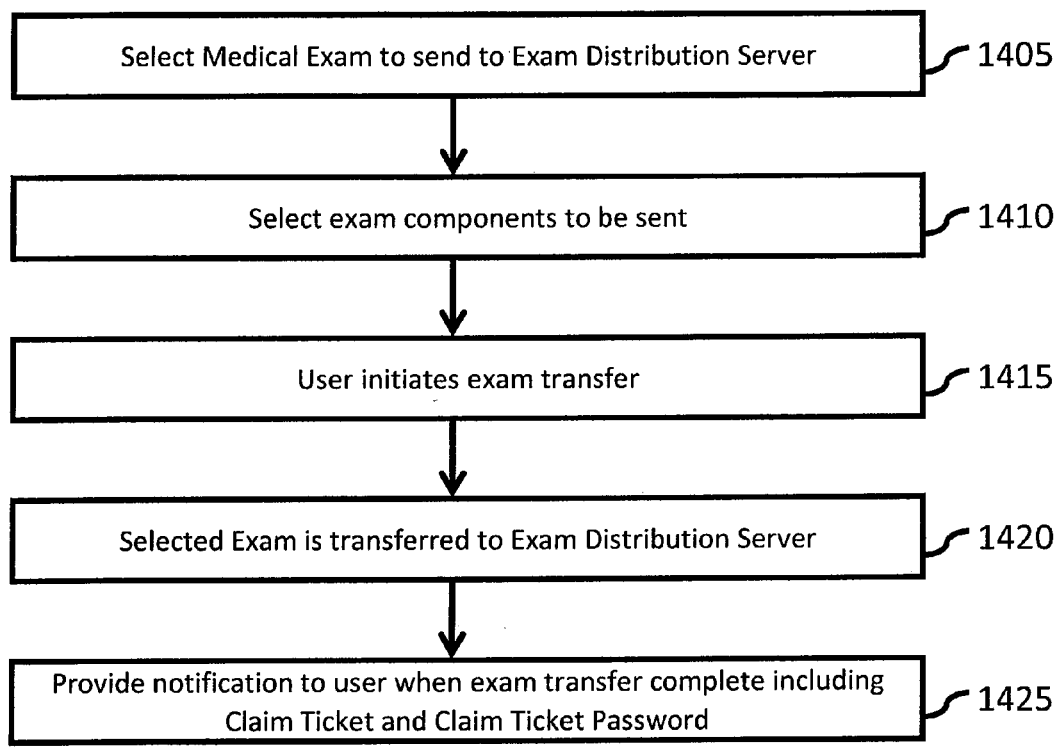
FIG. 12 is a block diagram illustrating an exam workflow for uploading and sending according to a second embodiment of the present invention.

Turning now to FIG. 12, a workflow diagram describing the method for a user to send an exam is shown. In this example the sending computer is, for example, a PACS system and the functionality described here could be completely integrated into a PACS system. Alternatively, the described functionality could be present in a combination of a PACS system and separate client software interfaced with the PACS system, for example using industry standard communications protocols such as DICOM.

Figure 16:
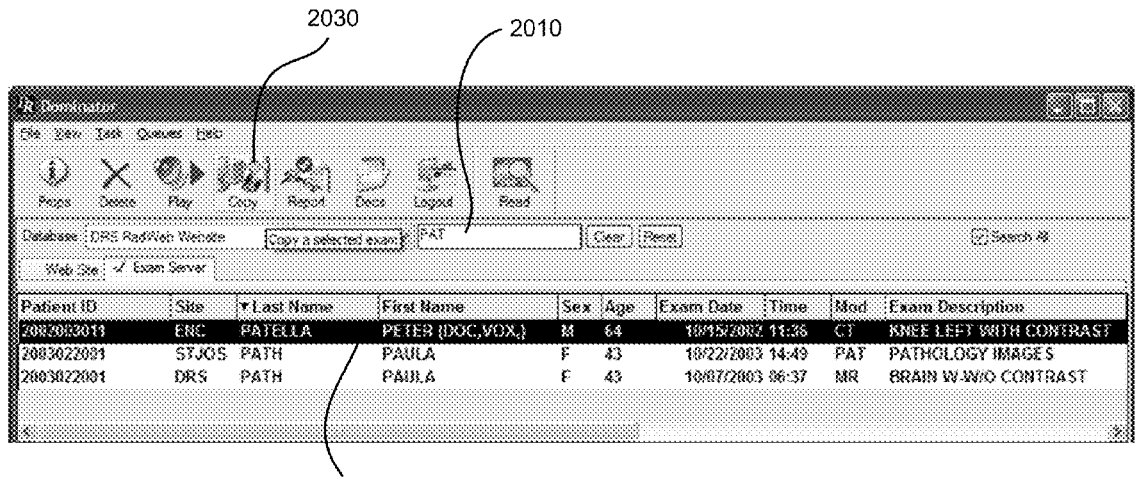
FIG. 16 is an example of a graphical user interface (GUI) for selecting an exam for use in the second embodiment of the present invention as shown in FIGS. 12 and 13.

The user selects a medical exam to send, as shown in block 1405 of FIG. 12. An example of a GUI that could be used to select an exam is shown in FIG. 16. The selected exam could reside within a medical information system such as a PACS or EMR (Electronic Medical Record) System or could be stored on a CD, DVD, or other media. In the example GUI shown in FIG. 16, an exam is selected by typing one more characters into a search field 2010, which displays a list of patients having matching names or medical record numbers. The user then clicks the "Copy" button 2030 to initiate the copy function.

Figure 17:
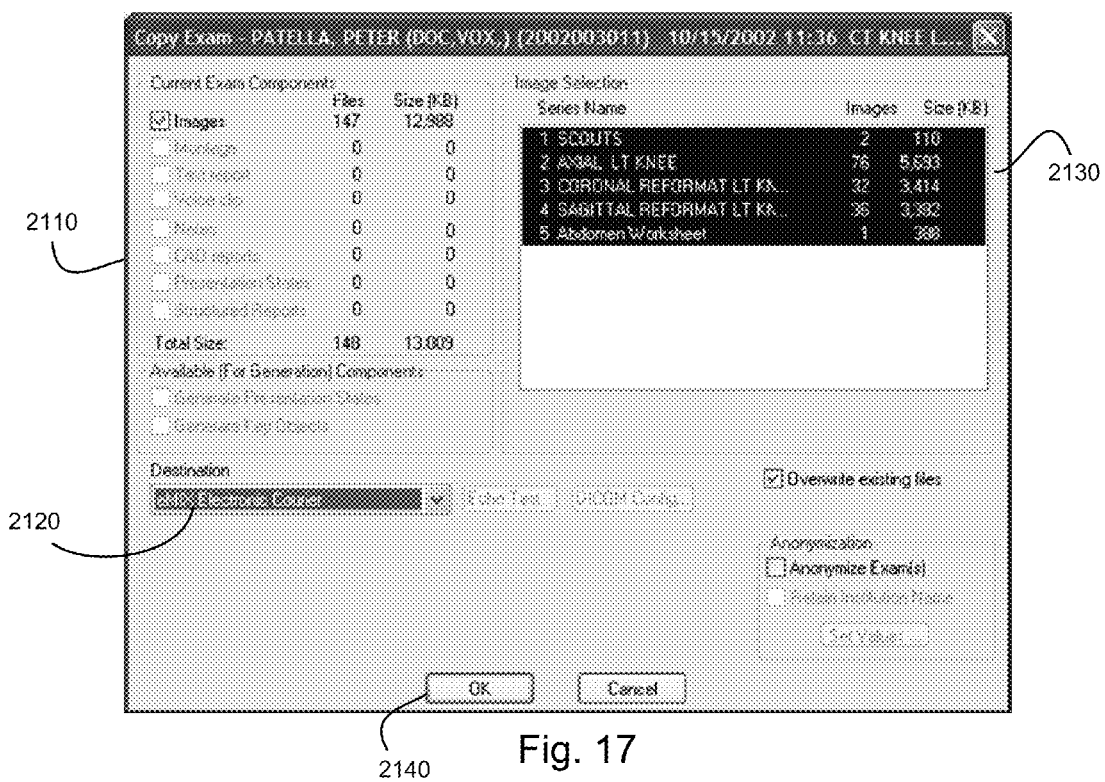
FIG. 17 is an example GUI to facilitate a user copying an exam for use in the second embodiment of the invention as shown in FIGS. 12 and 13.
Figure 18:
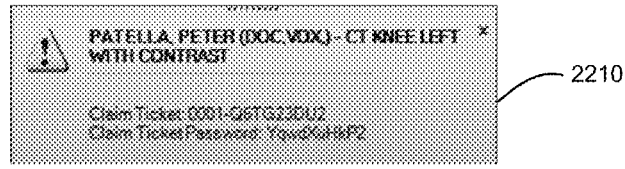
FIG. 18 is an alert box element of a GUI used to convey information to a user for use in the second embodiment of the invention as shown in FIGS. 12 and 13.
Figure 19:
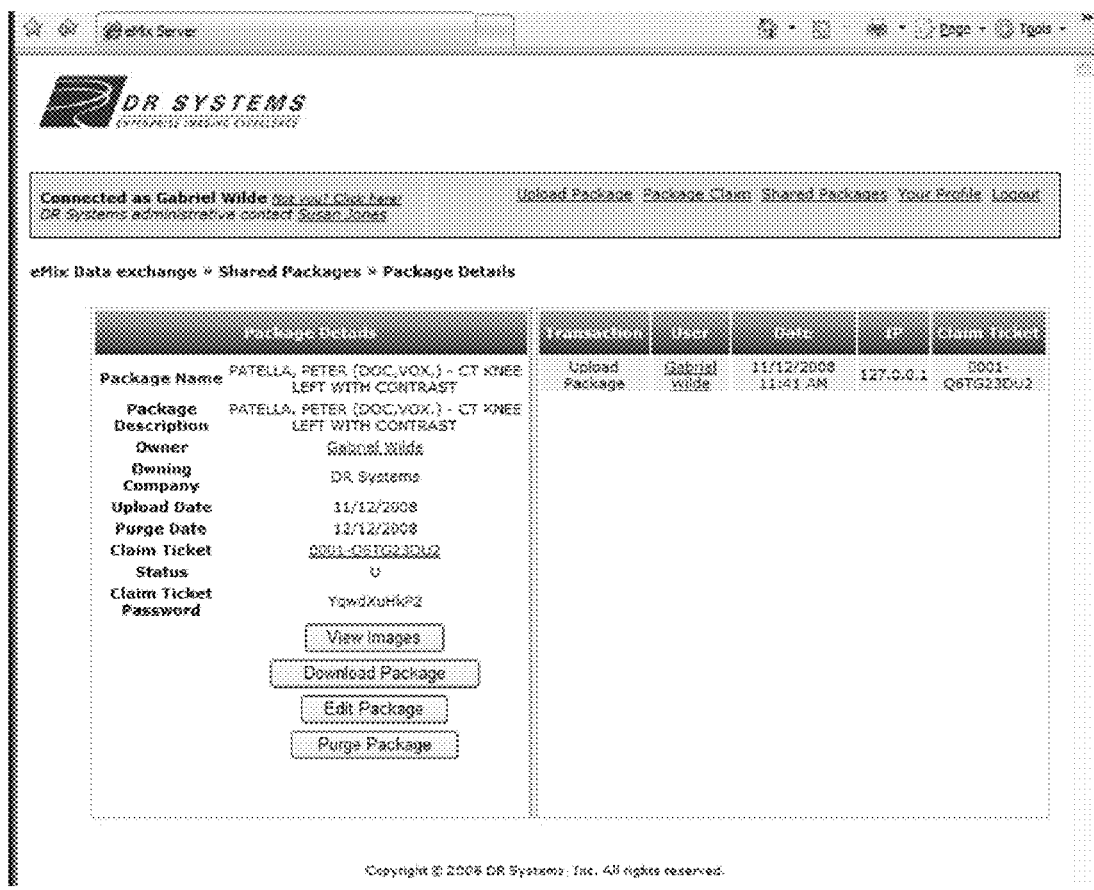
FIG. 19 is an example of a web page used to display package details for use with the second embodiment of the present invention as shown in FIGS. 12 and 13.

Selecting "Copy" results in the display of the "Copy Exam" dialog box illustrated in FIG. 17. The user then selects the Exam components to be sent, as shown in FIG. 12, block 1410. This is accomplished by interacting with the GUI is shown in FIG. 17 which shows the Copy Exam dialog box 2110. For electronic transfer using the system being described, the user selects "eMix Electronic Courier" as the Destination in destination selection box 2120, and selects Exam components to be sent by highlighting them in list 2130.

Once exam components to be sent are selected, the user clicks the "OK" button 2140 of GUI 2110 to initiate transfer, block 1415 of FIG. 12. The selected exam is then transferred to the exam distribution server, as shown in block 1420 of FIG. 12.

When the exam is fully copied to the exam distribution server, a notification alerts the user that the Exam has been posted at block 1425 of FIG. 12. The alert dialog box preferably includes information identifying the posted exam and how the exam can be retrieved. An example notification is illustrated by the alert dialog box 2210 in FIG. 18. The alert dialog box 2210 includes a Claim Ticket and a Claim Ticket Password, which can be communicated to another user so that he can download or view the exam.

The user may click the alert dialog 2210 or dismiss this alert. If the user clicks the alert box 2210, a web browser will be opened to display a web page containing details regarding the package stored on the exam distribution server, as illustrated by the web page shown in FIG. 19.

Figure 13:
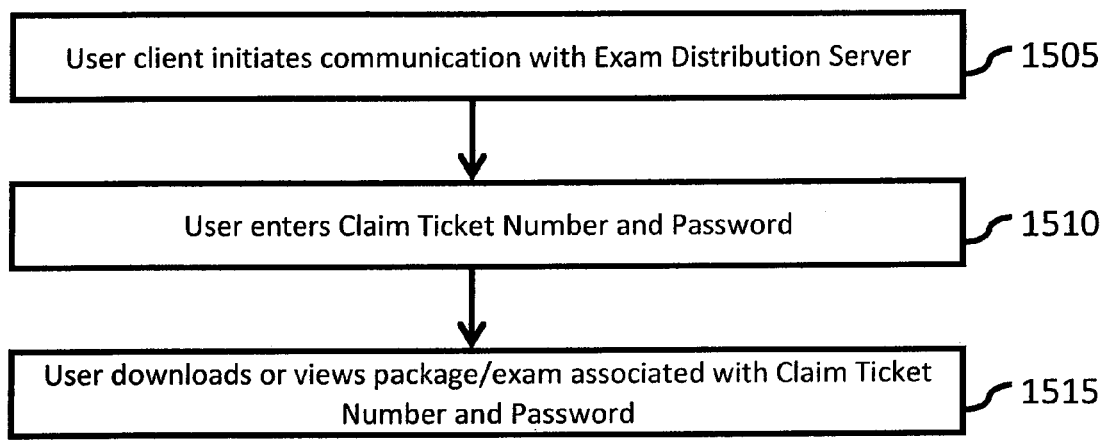
FIG. 13 is a block diagram illustrating an exam workflow for receiving and viewing according to the second embodiment of the present invention.

Turning now to FIG. 13, the workflow describing the steps required for a user to receive or view an exam are shown. In order to receive or view an exam, the user initiates communication with the exam distribution server, as shown in block 1505 of FIG. 13. This is accomplished through use of an internet browser or other client software.

Figure 20:
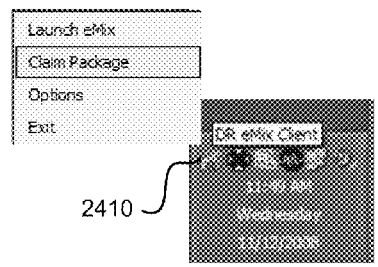
FIG. 20 is an example of a taskbar icon for use with the second embodiment of the present invention as shown in FIGS. 12 and 13.

FIG. 20 is an example GUI showing how a client could be launched to initiate communication with the exam distribution server to claim a package. When the user clicks on a taskbar icon 2410 labeled "DR eMix Client," a menu containing a list of options is displayed including, for example, options to launch the client, claim a package, configure the client, or exit the client. It will be appreciated by those of skill in the art that more or fewer options could be available to a user without departing from the spirit of the invention. It will also be appreciated that the option titles shown in FIG. 20 are merely for illustrative purposes, and that other titles could be substituted for those shown.

Figure 21:
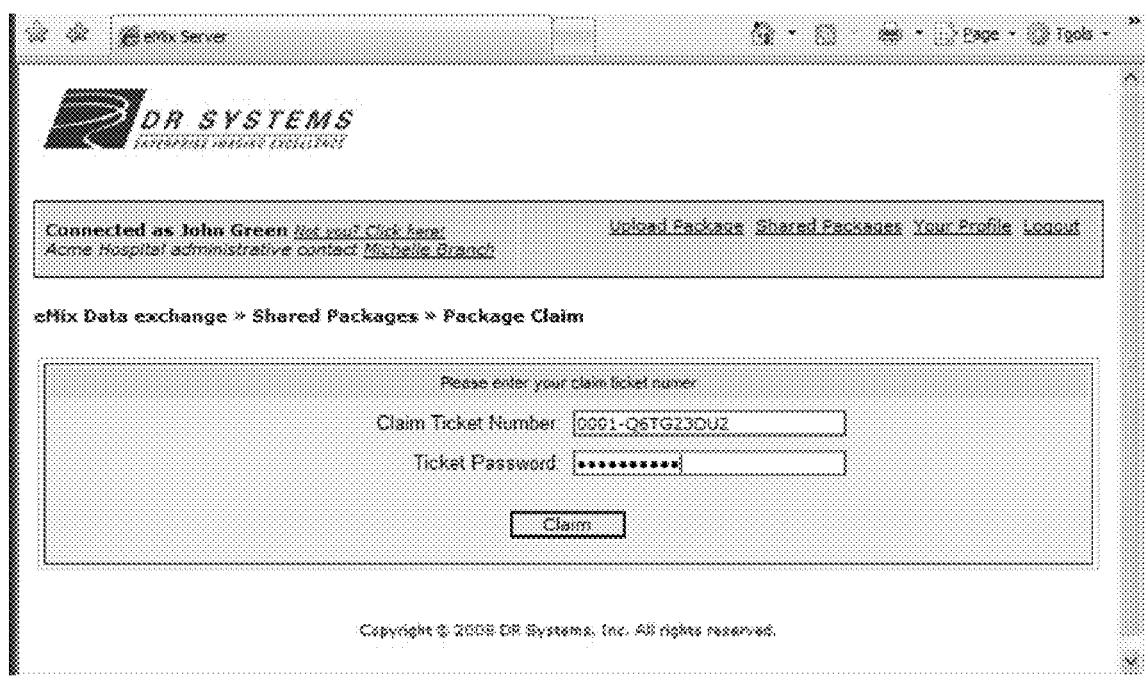
FIG. 21 is an example of a GUI to facilitate a claim ticket retrieval process for use with the second embodiment of the present invention as shown in FIGS. 12 and 13.

When a user selects the "Claim Package" option from the menu, the user is connected to the exam distribution server website. Once connected, the user enters the Claim Ticket Number and Claim Ticket Password for the desired exam, as indicated in block 1510 of FIG. 13. An example GUI for facilitating the user's data entry is shown in FIG. 21, where the user would enter the Claim Ticket Number and Ticket Password, and then select the "Claim" button.

After entering the claim information, the user can view or download the specified package/exam, as shown in FIG. 13 block 1515. The user is presented with the GUI shown in FIG. 22, which displays information related to the exam, here referred to as a package. Using buttons on the web page, the user can view any images contained in the exam, download the exam, or purge the exam by clicking the "View Images," "Download Package," or "Purge Package" buttons, respectively.

Figure 22:
FIG. 22 is an example of a GUI displaying exam information for use with the second embodiment of the present invention as shown in FIGS. 12 and 13.
Figure 23:
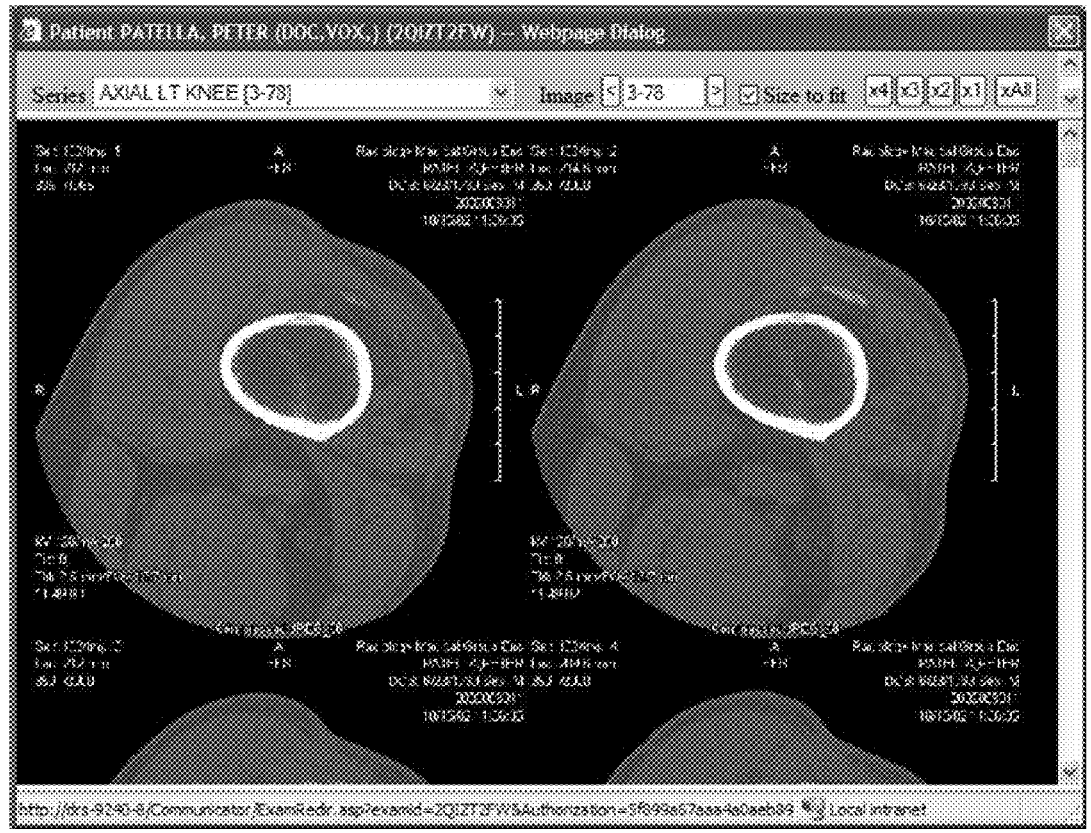
FIG. 23 is an example of an exam image viewed according to the second embodiment of the present invention as shown in FIGS. 12 and 13.

When the user chooses to view the images by selecting the "View Images" button of the GUI illustrated in FIG. 22, he can view the exam images within a web browser, as shown in FIG. 23. Alternatively, in response to the user selecting the "View Images" button, another program on the user's computer may be launched to provide exam viewing functionality.

Figure 14:
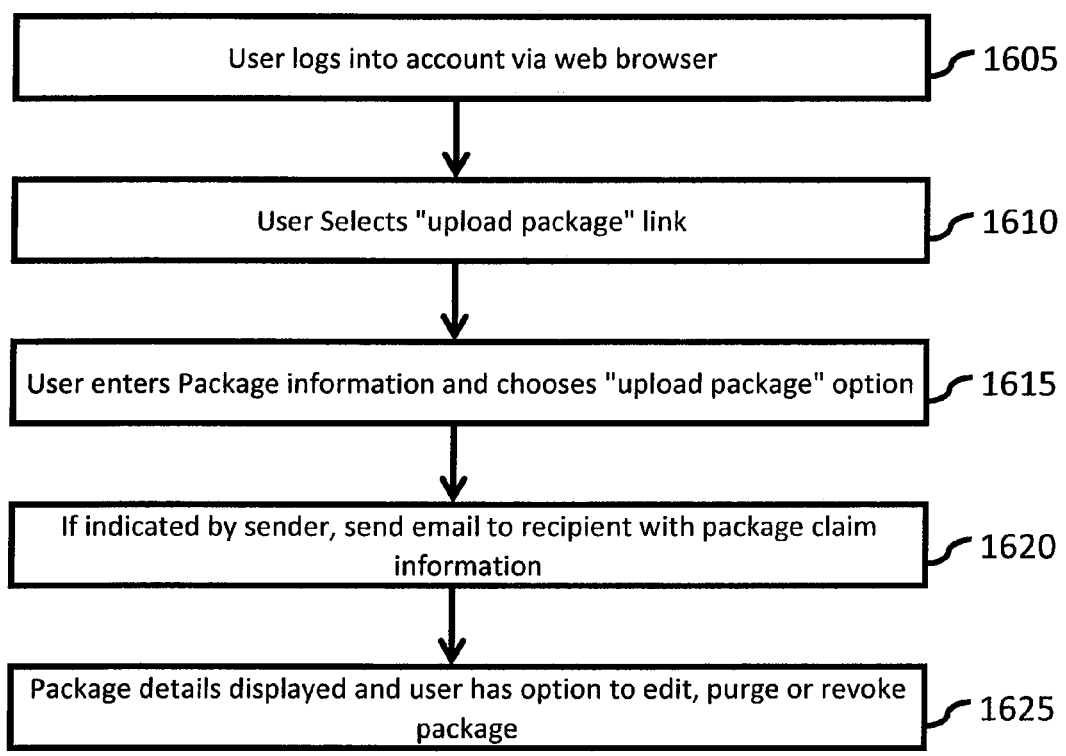
FIG. 14 is a block diagram illustrating a workflow for package uploading and sending according to a third embodiment of the present invention.

A third embodiment related to file/package workflow will now be described with reference to FIGS. 14, 15, and 24-32. Turning now to FIG. 14, a workflow describing the steps required for a user to send a "package" (i.e., a file that contains the contents of one or more files) is shown.

Figure 24:
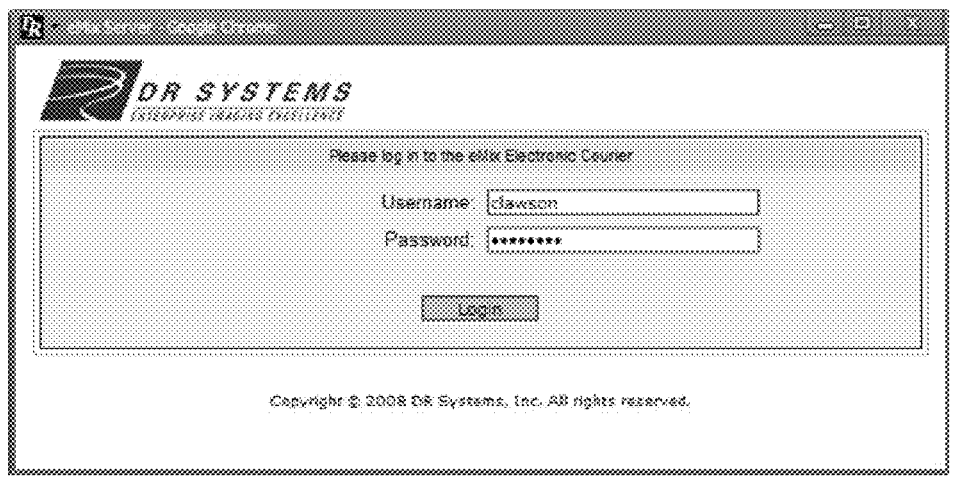
FIG. 24 is a GUI facilitating a user login process for use with the third embodiment of the present invention as shown in FIGS. 14 and 15.

The user first logs into his account on the Exam Distribution Server, as shown in block 1605 of FIG. 14. An example GUI facilitating a login step utilizing a web browser is illustrated in FIG. 24. Alternatively, the user could log in through a standalone software client. In response to logging in, the user is presented with a series of options, as shown in the GUI of FIG. 25.

Figure 25:
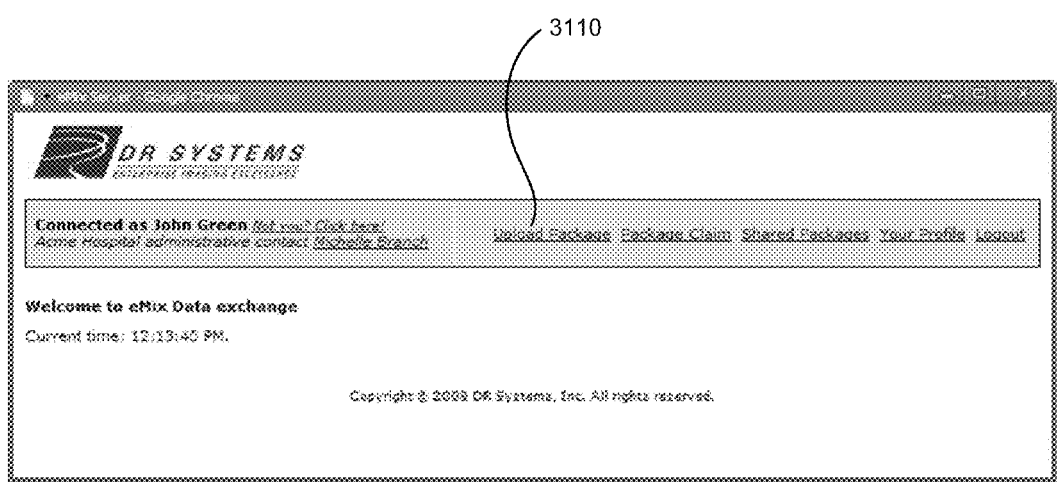
FIG. 25 is a GUI facilitating package upload for use with the third embodiment of the present invention as shown in FIGS. 14 and 15.
Figure 26:
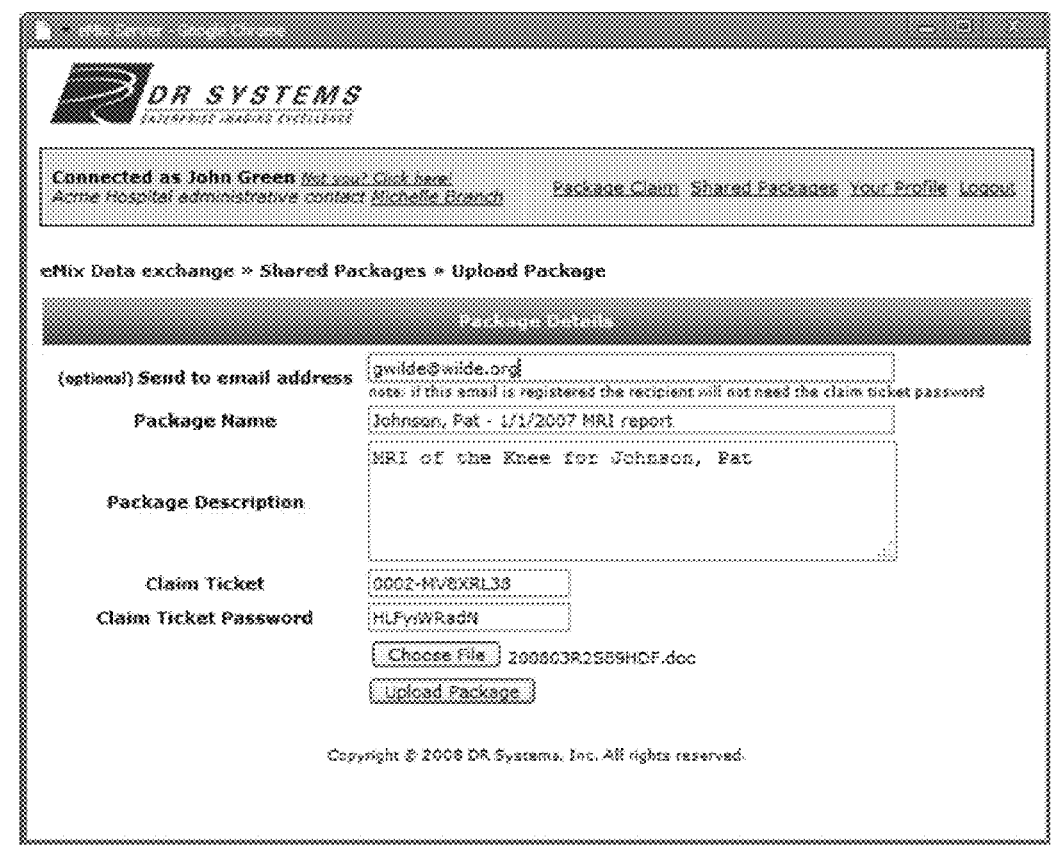

To upload a package as shown in block 1610 of FIG. 14, the user selects "upload package" item 3110 of FIG. 25. The user then enters information identifying the package to be sent in step 1615 of FIG. 14. An exemplary interface for this step is illustrated in FIG. 26. The user clicks a "Choose File" button and is presented with a dialog that allows the user to select a file. Preferably, the user also enters an email address to provide a package notification email to the entered email address. If an email address is entered and the recipient has an account on the system, the package is delivered directly to his account. If the recipient does not have an account on the system, the recipient will be able to create a guest account only with a valid Claim Ticket and Claim Ticket Password.

To upload the package, the user clicks the "Upload Package" button in the GUI of FIG. 26. If an email address is provided in the GUI of FIG. 26, an email with the package information including at least the Claim Ticket is sent to the provided email address, as shown in block 1620 of FIG. 14. Additionally, a claim ticket password may be communicated to the recipient using a secure transfer means, as shown in block 1710 of FIG. 15. However, the recipient will not require a claim ticket password if he is has a registered account on the exam distribution server.

Figure 27:
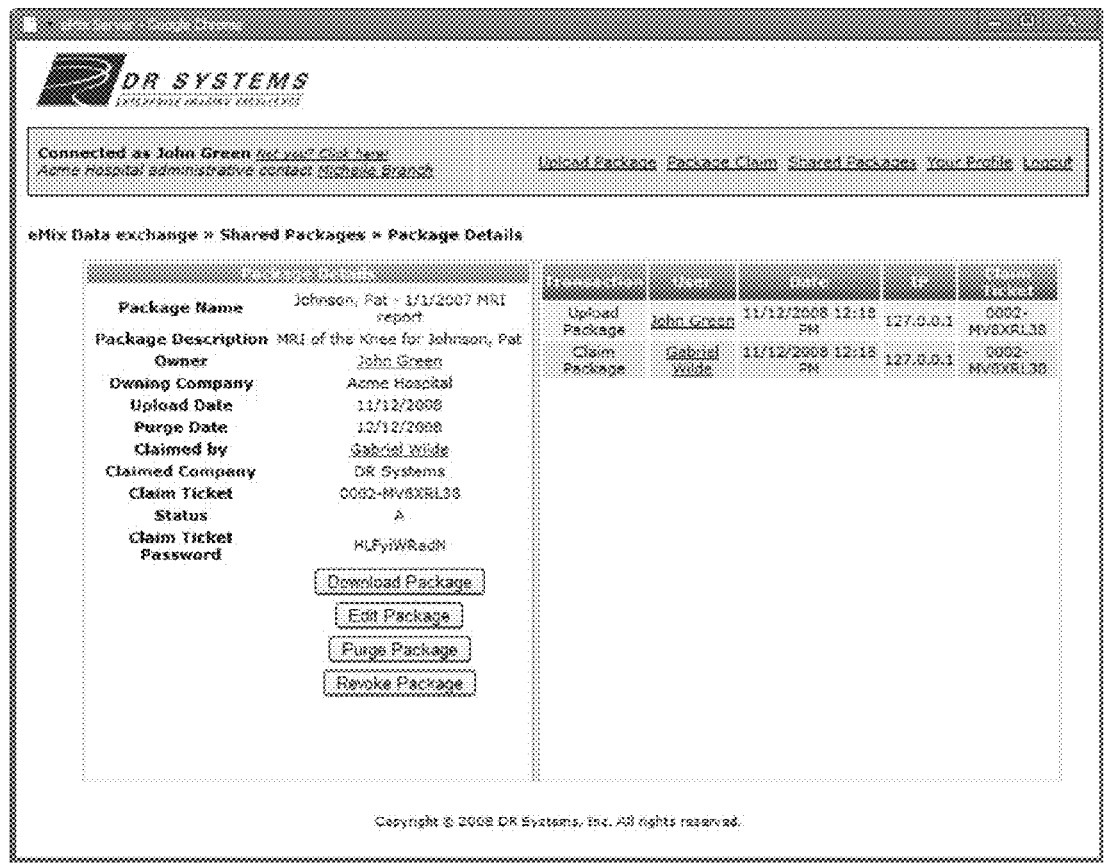
FIG. 27 is a screenshot displaying detail information for an uploaded package for use with the third embodiment of the present invention as shown in FIGS. 14 and 15.

After uploading the package, the sending user is redirected to the Package details page shown in FIG. 27, with options to edit, purge, or revoke the package, as shown in block 1625 of FIG. 14. Within the Package details page of FIG. 27, the "Edit Package" button will allow the Package Name/Description/Purge date to be modified. The "Purge Package" button will allow the user to purge the package contents to prevent downloading the package, but will not remove the package details and audit transaction. The "Revoke Package" button will remove the ability of the claiming user to see the package or download the package contents from that point forward. When a package is revoked, the system preferably generates a new claim ticket password so that the package can be claimed by another user.

Figure 15:
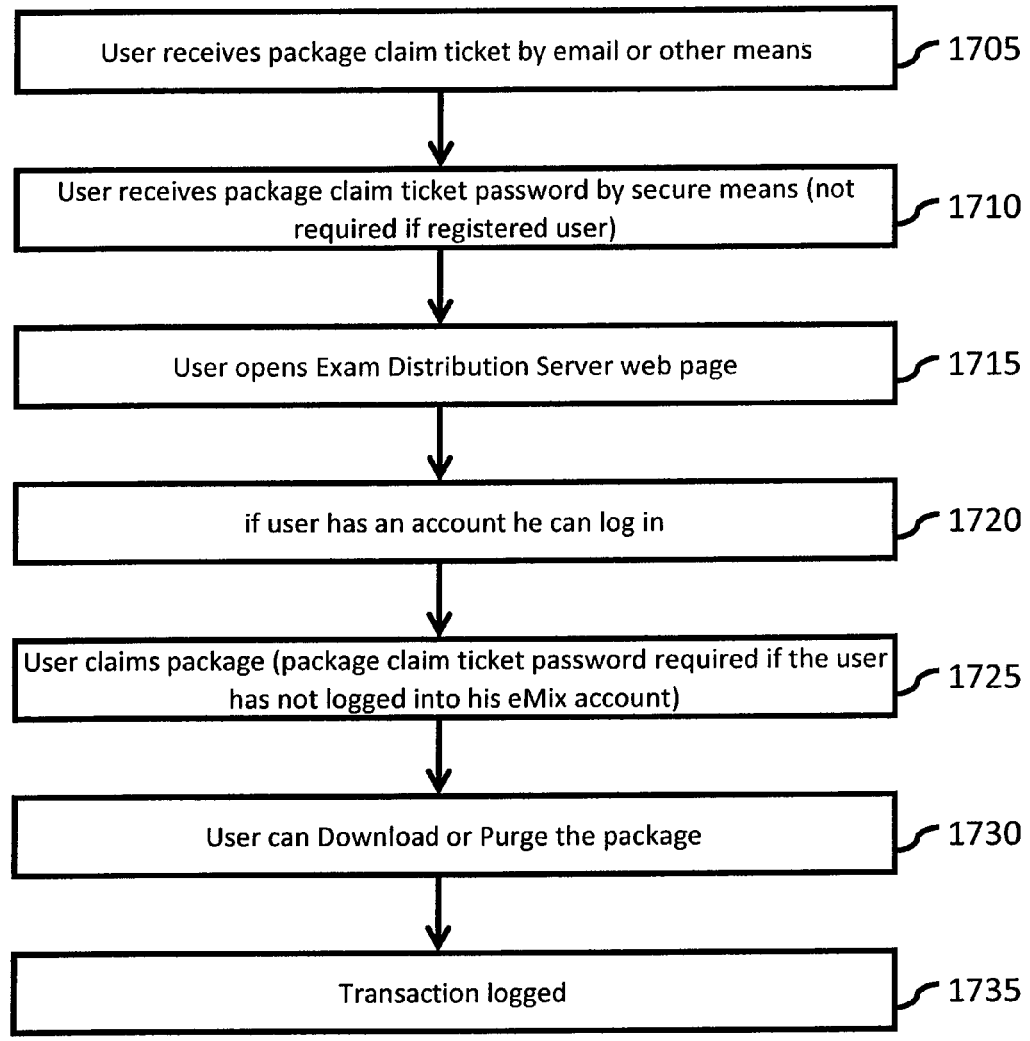
FIG. 15 is a block diagram illustrating a workflow for package receiving and downloading according to the third embodiment of the present invention.
Figure 28:
FIG. 28 is a screenshot displaying an example email message received by a user when the user receives a package in the third embodiment of the present invention as shown in FIGS. 14 and 15.
Figure 29:
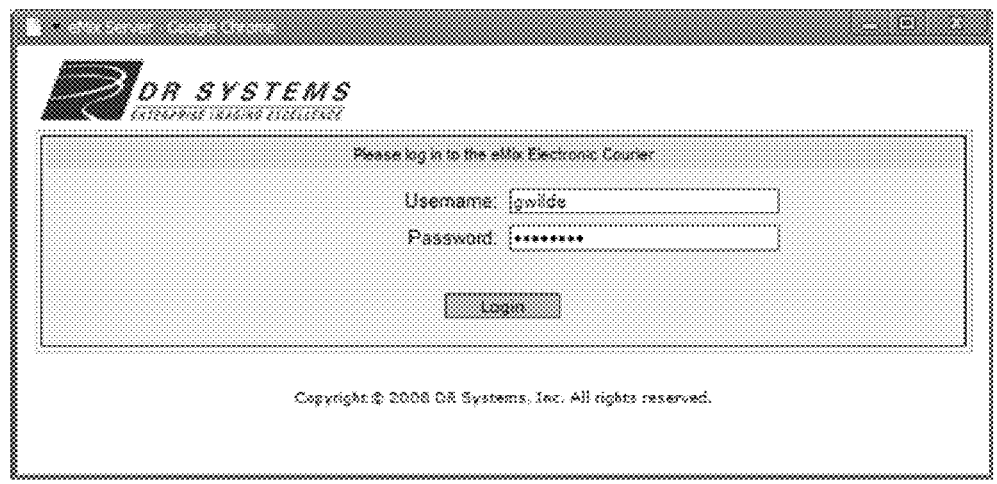
FIG. 29 is a GUI facilitating the login of a user for use with the third embodiment of the present invention as shown in FIGS. 14 and 15.

Turning now to FIG. 15, a workflow describing steps required for a user to receive a package is shown. A receiving user receives an email or other message containing a claim ticket number and a web site link to claim the package as shown in block 1705 of FIG. 15. An example email communication containing the claim ticket number and the link is shown in FIG. 28. Additionally, a claim ticket password is preferably communicated to the recipient using a secure transfer means, as shown in block 1710 of FIG. 15. The claim ticket password is not required if the package is sent to a user with a registered account registered on the exam distribution server.

Figure 30:
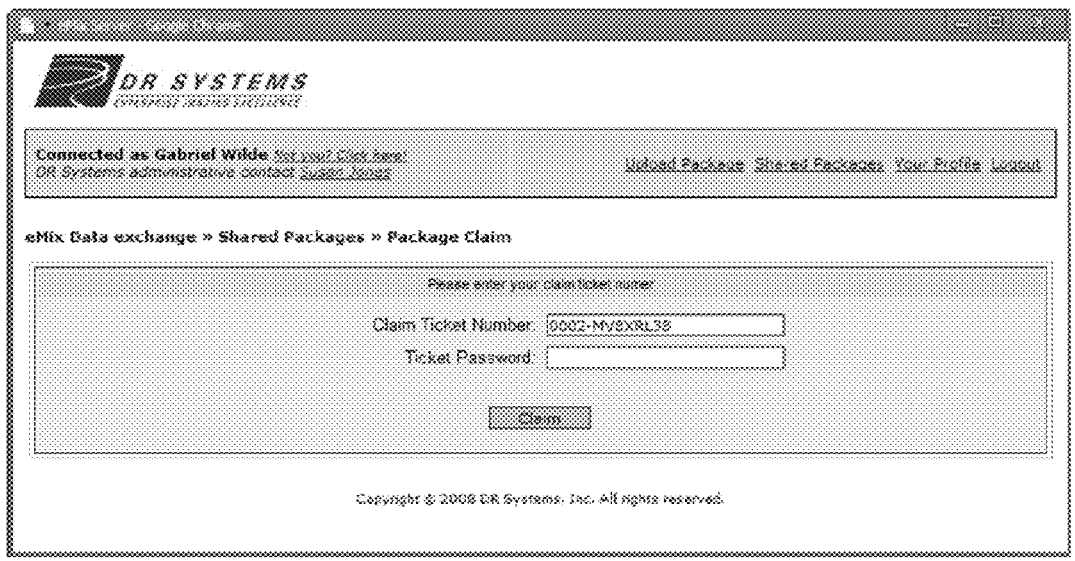
FIG. 30 is a GUI facilitating a user's entry of claim ticket information to retrieve a package for use with the third embodiment of the present invention as shown in FIGS. 14 and 15.

The receiving user navigates to a web page on the exam distribution server, as shown in block 1715 of FIG. 15. This can be accomplished, for example, by clicking on the link provided in example email message shown in FIG. 28. If the receiving user clicks the provided link in the email, a GUI for entry of the Claim ticket number and ticket password will be presented to the user, as illustrated in FIG. 30. Alternatively, as shown in block 1720 of FIG. 15, the user may login to the system using the GUI of FIG. 29. After logging in, the user selects the Claim Package link on the main eMix web page as shown in block 1725 of FIG. 15. To claim the package, the user enters at least the claim ticket number associated with the package. If the user does not receive packages directly into a registered account, the user must enter both the claim ticket number and password to claim the package.

Figure 31:
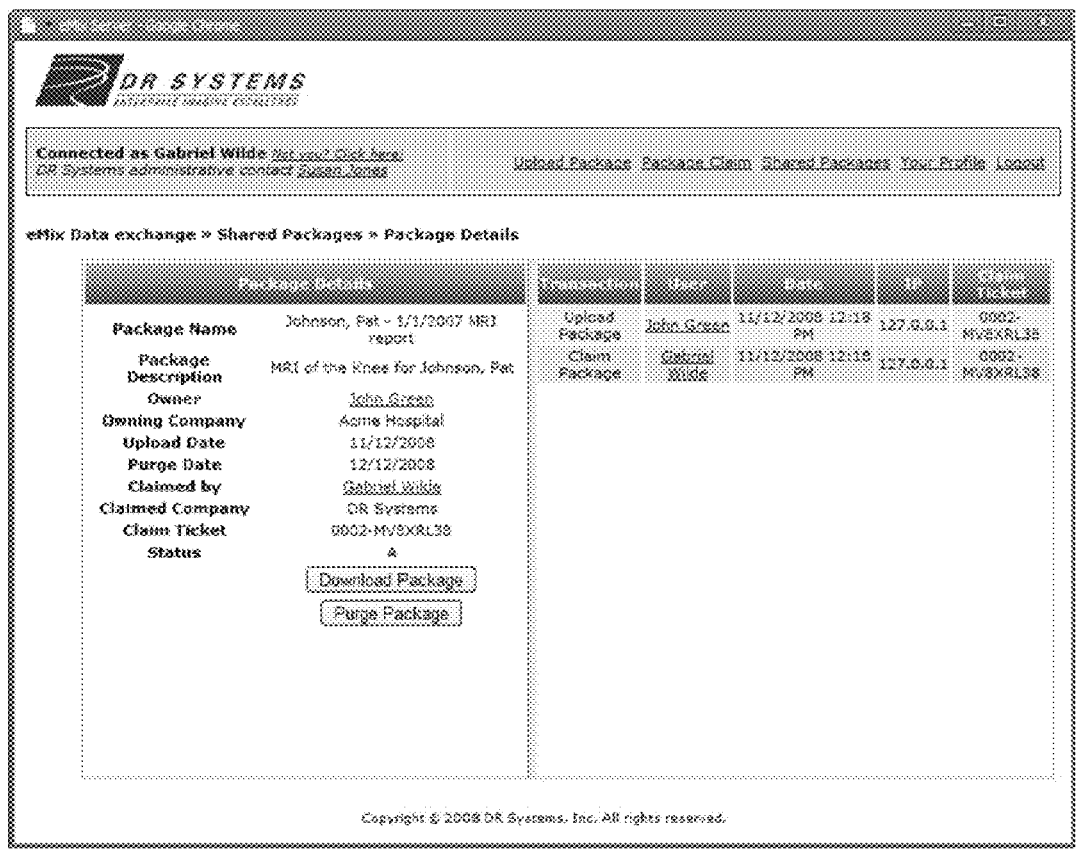
FIG. 31 is a screenshot showing package details for a package that a user receives in a third embodiment of the present invention as shown in FIGS. 14 and 15.
Figure 32:
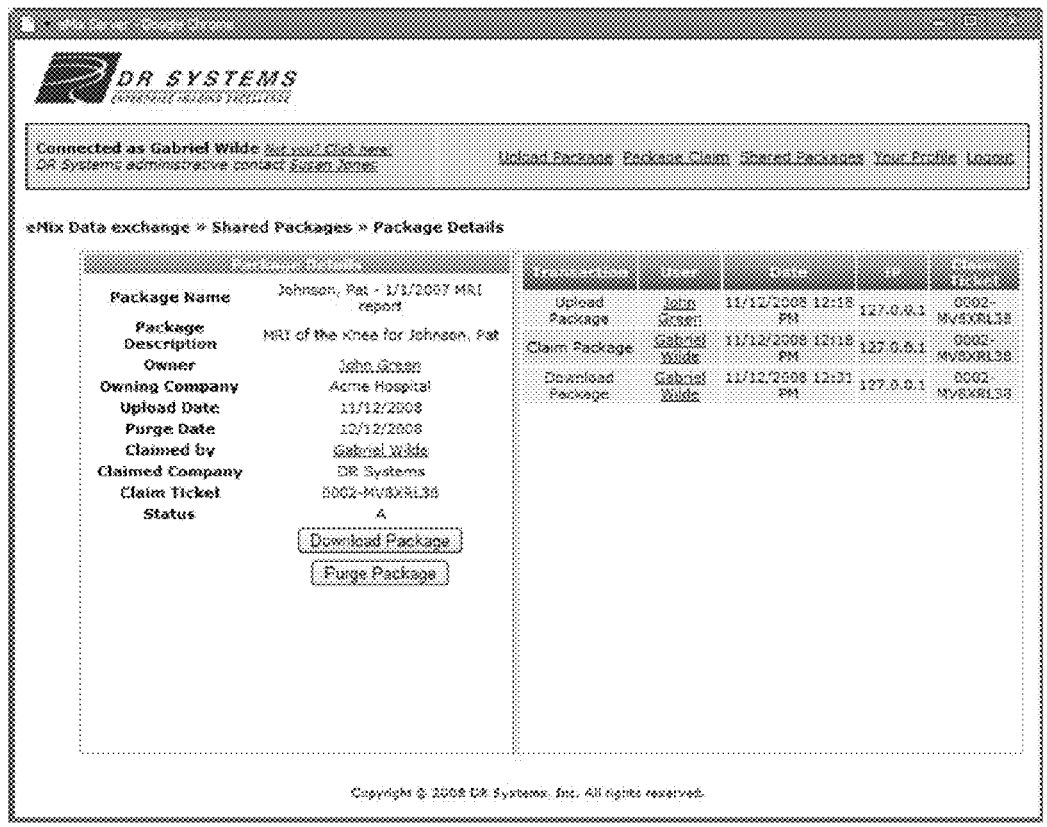
FIG. 32. is a screenshot showing a transaction audit log of a transaction according to the third embodiment of the present invention as shown in FIGS. 14 and 15.

Once the package is claimed, for example by the user clicking the "claim" button in FIG. 30, the receiving user is redirected to a Package Details page, as shown in FIG. 31. Depending on the sending user's policy settings, the receiving user has the option to Download or optionally purge the package using the "Download Package" or "Purge Package" buttons, respectively, as shown in FIG. 15, block 1730. The user's transaction is logged in the transaction audit log, as shown in block 1735 of FIG. 15. The transaction audit log can be displayed, as shown on the web page illustrated in FIG. 32.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A system for transferring medical records from one or more source locations to one or more destination locations, the source locations and destination locations selected from a plurality of medical site clients connected via a network, each of which has access to medical records at a corresponding medical site, the system comprising:

at least one request initiating client device configured to generate simultaneously an exam transfer request specific to the medical records desired and an exam transfer authorization that authorizes the transfer of the medical records, an exam distribution server configured to be connectable to each of the plurality of medical site clients via the network, the exam distribution server configured to receive the exam transfer request and to receive the corresponding exam transfer authorization, wherein said exam transfer request specifies exam criteria and the one or more destination locations to which medical exams that have the criteria should be transferred and a desired format of the records, wherein, upon receipt of the exam transfer request and the exam transfer authorization, the exam distribution server forwards the request and the authorization to the one or more source location medical site clients, wherein one or more source location medical site clients are configured to accept the exam transfer authorization and grant access to records authorized in the exam transfer authorization and stored at the source location medical site;

wherein, the exam distribution server receives all exam records meeting the criteria of the exam transfer request from the source location medical site clients as a response to the forwarded request and exam transfer authorization, wherein the exam distribution server periodically receives a list of recent exams from each of the medical site clients and wherein the exam distribution server generates a data package containing all of the records that meet the request and are authorized by the authorization and subsequently forwards received the package containing the exam records to the one or more destination locations specified in the exam transfer request.

2. The system of claim 1, the exam distribution server further configured to be connectable to a doctor client via the network.

3. The system of claim 1, the exam distribution server further configured to be connectable to a patient client via the network.

4. The system of claim 1, wherein the exam distribution server is configured to receive the exam transfer authorization from each of a patient client, a doctor client, and the medical site client.

5. The system of claim 4, wherein the exam transfer authorization is stored by the exam distribution server.

6. The system of claim 4, wherein the exam distribution server receives the exam transfer request from one of a doctor client and the one or more medical site clients.

7. The system of claim 1, wherein the criteria include one or more of a patient name, a medical record number, a range of dates, an ordering doctor, a modality, an anatomic region examined, an exam type, and an abnormal result.

8. The system of claim 1, wherein the exam distribution server stores a log of exam activity, including exam uploads, exam downloads, and exam views.

9. The system of claim 1, wherein each of the medical site clients comprises a medical information system that stores exam records, and wherein the exam records include one or more of medical images, a medical report, patient demographic information, patient identification information, insurance information, and doctor orders.

10. The system of claim 1, wherein the exam distribution server stores received exam transfer requests, and wherein the server checks the received lists of recent exams from the plurality of medical client sites to determine if the exams meet the criteria included in the stored exam transfer requests.

11. The system of claim 1, wherein the exam transfer authorization specifies one or more authorized destination locations that are authorized to receive an exam record, the exam distribution server forwarding an exam record specified in an exam transfer request only when each the one or more destination locations specified in the exam transfer request is also specified as an authorized destination location in the exam transfer authorization.

12. A method of transferring medical records from one or more sources to a destination using a computer system including a plurality of medical site clients, one or more patient clients, and one or more doctor clients, connected to an exam distribution server via a network, the method comprising the steps of:

generating an exam transfer request directed to a given set of medical records and generating a corresponding transfer authorization for the given set of medical records;

receiving the exam transfer request and the corresponding exam transfer authorization at the exam distribution server, the exam transfer request specifying exam criteria and the destination to which medical exams that meet the specified criteria should be transferred and a desired format of the records;

transmitting the exam transfer request and the corresponding exam transfer authorization from the exam distribution server to each of the medical site clients in response to the exam distribution server receiving the exam transfer request and the corresponding exam transfer authorization;

granting access to records authorized in the exam transfer authorization and stored at the source location medical site;

receiving, at the exam distribution server, exams that satisfy the exam transfer request criteria and corresponding exam transfer authorization from the one or more medical site clients, wherein the exam distribution server periodically receives a list of new exams from each of the medical site clients;

generating, by the exam distribution server, a data package containing all the medical records received from the medical site clients; and transferring the data package containing all the matching exams from the exam distribution server to the destination indicated in the exam transfer request.

13. The method of claim 12, further comprising a step of notifying, via the exam distribution server, the patient client and/or the doctor client that an exam transfer was completed.

14. The method of claim 12, further comprising a step of communicating the exam distribution server receiving an exam transfer request acknowledgement from each of the medical site clients in response to the medical site client receiving an exam transfer request.

15. The method of claim 14, wherein the exam transfer request acknowledgement includes information indicating whether or not exams matching the criteria in the exam transfer request were located and whether or not the located exams were communicated to the distribution server successfully.

16. The method of claim 12, wherein the exam distribution server receives the exam transfer request is communicated to the exam distribution server by from the destination computer.

17. The method of claim 12, wherein the exam distribution server receives the exam transfer request is communicated to the exam distribution server by from the source computer.

18. The method of claim 12, wherein the exam distribution server receives the exam transfer request is communicated to the exam distribution server by from one of the doctor client, the patient client, and the medical site client.

19. The method of claim 12, wherein the exam distribution server maintains a log of exam transfer activity, including exam uploads, exam downloads, and exam views.

20. The method of claim 12, wherein the exam distribution server saves received exam transfer requests, and
wherein when the exam distribution server receives a list of new exams from any of the medical site clients, the server compares the exams to the saved exam transfer requests to determine if the exams meet the criteria of the exam transfer requests.

21. The method of claim 12, wherein the exam distribution server receives the exam transfer authorization from the patient client.

22. The method of claim 21, wherein the exam distribution server receives the exam transfer request from one of the plurality of medical site clients or the one or more doctor clients.

23. A non-transitory computer-readable medium storing which, when executed, causes a computer to execute an exam distribution server process comprising steps of:
conducting an imaging exam on a patient;
automatically generating an exam transfer request directed to a given set medical records and generating a corresponding transfer authorization for the given set of medical records;
receiving, from one of a plurality of medical site clients, one or more medical exam components and a recipient identification along with the exam transfer request and the corresponding exam transfer authorization at a exam distribution server, the exam transfer request specifying exam criteria and a destination to which medical exams that meet the specified criteria should be transferred and a desired format of the records;
transmitting the exam transfer request and the corresponding exam transfer authorization from the exam distribution server to each of the medical site clients in response to the exam distribution server receiving the exam transfer request and the corresponding exam transfer authorization;
granting access to records authorized in the exam transfer authorization and stored at a source location medical site;
receiving, at the exam distribution server, exams that satisfy the exam transfer request criteria and corresponding exam transfer authorization from the one or more medical site clients, wherein the exam distribution server periodically receives a list of recent exams from each of the medical site clients;
generating a data package containing all the medical records received from the medical site clients; and
generating a claim ticket and password related to the generated data package containing the received medical exam components; and
sending the data package, the claim ticket and password to the identified recipient.

24. The non-transitory computer-readable medium of claim 23, the exam distribution server process further comprising steps of:
receiving a claim ticket and password from another client; and
transmitting the data package containing one or more medical exam components associated with the received claim ticket and password to the other client.

* * * * *